(12) United States Patent
Tsuruta et al.

(10) Patent No.: US 8,997,324 B2
(45) Date of Patent: Apr. 7, 2015

(54) TUBE CLAMPING DEVICE AND HYDRAULIC PRESSURE TESTER TECHNICAL FIELD

(75) Inventors: Satoshi Tsuruta, Osaka (JP); Katsuhiko Ito, Osaka (JP); Katsumi Ishigaki, Osaka (JP); Hiroaki Yabuta, Osaka (JP)

(73) Assignee: Nakata Manufacturing Co., Ltd., Osaka-shi (JP)

( * ) Notice: Subject to any disclaimer, the term of this patent is extended or adjusted under 35 U.S.C. 154(b) by 0 days.

(21) Appl. No.: 14/127,281

(22) PCT Filed: Jul. 1, 2011

(86) PCT No.: PCT/JP2011/065220
§ 371 (c)(1),
(2), (4) Date: Mar. 11, 2014

(87) PCT Pub. No.: WO2013/005283
PCT Pub. Date: Jan. 10, 2013

(65) Prior Publication Data
US 2014/0238111 A1 Aug. 28, 2014

(51) Int. Cl.
| | |
|---|---|
| B25B 27/14 | (2006.01) |
| G01N 3/02 | (2006.01) |
| G01M 5/00 | (2006.01) |
| B25B 5/12 | (2006.01) |
| B25B 5/14 | (2006.01) |
| G01N 3/12 | (2006.01) |

(52) U.S. Cl.
CPC .............. *G01N 3/02* (2013.01); *G01M 5/0058* (2013.01); *B25B 5/12* (2013.01); *B25B 5/147* (2013.01); *G01N 3/12* (2013.01)

(58) Field of Classification Search
USPC ................. 29/91, 92, 93, 218, 270, 281.1
See application file for complete search history.

(56) References Cited

U.S. PATENT DOCUMENTS

| | | | | |
|---|---|---|---|---|
| 7,121,166 B2 * | 10/2006 | Drzewiecki | ............ | 81/57.33 |
| 8,496,238 B1 * | 7/2013 | Orgeron | ............ | 269/270 |
| 2010/0187740 A1 * | 7/2010 | Orgeron | ............ | 269/218 |

FOREIGN PATENT DOCUMENTS

| | | |
|---|---|---|
| JP | 50 146391 | 11/1975 |
| JP | 63 206629 | 8/1988 |

(Continued)

OTHER PUBLICATIONS

International Search Report Issued Sep. 13, 2011 in PCT/JP11/065220 Filed Jul. 1, 2011.

*Primary Examiner* — Lee D Wilson
*Assistant Examiner* — Shantese McDonald
(74) *Attorney, Agent, or Firm* — Oblon, Spivak, McClelland, Maier & Neustadt, L.L.P.

(57) ABSTRACT

A compact tube clamping device for inspecting an electric resistance welded tube quality. A lifting/lowering base including a tube support body is provided onto a fixed base. Clamp claws sandwich the tube support body. A claw drive body lifting/lowering independently of the lifting/lowering base is provided in the lifting/lowering base. Opposite side portions of the claw drive body are connected to opposite clamp claws by links to turn the opposite clamp claws in closing directions by lowering with respect to the lifting/lowering base. A first drive mechanism for the lifting/lowering base and a second drive body for lifting/lowering the claw drive body are provided to the fixed base. A lowering stroke of the claw drive body necessary for closing operations of the clamp claws is partially born by lifting of the lifting/lowering base in transferring the tube, thereby suppressing the lowering stroke of the claw drive body.

12 Claims, 27 Drawing Sheets

(56) References Cited

FOREIGN PATENT DOCUMENTS

| | | |
|---|---|---|
| JP | 6 331061 | 11/1994 |
| JP | 8 71897 | 3/1996 |
| JP | 11 314879 | 11/1999 |
| JP | 2000 346278 | 12/2000 |
| JP | 2001 269833 | 10/2001 |

* cited by examiner

TUBE CLAMPING DEVICE AND HYDRAULIC PRESSURE TESTER TECHNICAL FIELD

TECHNICAL FIELD

The present invention relates to a tube clamping device suitably used for a hydraulic pressure tester for inspecting quality of an electric resistance welded tube and a hydraulic pressure tester using the tube clamping devices.

BACKGROUND ART

On a manufacturing line of electric resistance welded tube, a hydraulic pressure test is carried out to inspect quality of the manufactured electric resistance welded tube and especially quality of a welded part called a seam part. The hydraulic pressure test described here is carried out by pinching a predetermined length of manufactured electric resistance welded tube between a head stock and a tail stock disposed at front and back portions of a test line, sealing front and back opposite ends of the electric resistance welded tube, and injecting high-pressure water into the electric resistance welded tube through the head stock in this state. Pressure of the high-pressure water reaches about 90% of guaranteed strength and an electric resistance welded tube in which breakage of the welded part and a resultant burst of the tube do no occur is judged as a good-quality product in terms of mechanical strength.

With regard to a distinction between the head stock and the tail stock, a member for carrying out sealing of the tube end and injection and discharge of the high-pressure water is called a head stock and a member for carrying out sealing of the tube end and discharge of air in the tube is called a tail stock, in general. Both the stocks are movable in a front-back direction of the test line in order to conform to change in length of a tested tube and so that the tube end portions are inserted into both the stocks and sealed. Recently, the head stock for carrying out sealing of the tube end and injection and discharge of the high-pressure water is fixed and only the tail stock for carrying out sealing of the tube end and discharge of air in the tube is movable in some hydraulic pressure testers.

In such a hydraulic pressure tester for an electric resistance welded tube, fixing strength for resisting reaction force of the high-pressure water injected into the tested tube and fixed between the head stock for carrying out sealing of the tube end and injection and discharge of the high-pressure water and the tail stock for carrying out sealing of the tube end and discharge of air in the tube is required of both the stocks. Proposed from this point of view are an installed hydraulic pressure tester with both stocks firmly installed on a main frame, an embedded hydraulic pressure tester with both stocks embedded in a main frame, a coupled hydraulic pressure tester with both stocks coupled by tension beams, and the like.

These hydraulic testers have advantages and disadvantages. While the installed tester has an advantage that a space between both the stocks is open on upper and opposite sides to facilitate putting in and taking out of the tested tube, it has a disadvantage that, because both the stocks are cantilevered, a structure including the main frame is large and that a device is large in scale and weight. In the embedded tester, though the main frame can be made compact and lightweight, putting in and taking out of the tested tube are considerably restricted, because an open portion is formed only on an upper side. In the coupled tester, on the other hand, a tension rod can effectively receive a reaction force and therefore a device can be substantially reduced in scale and weight. Moreover, because a space between both the stocks is open on upper and opposite sides, a tested tube can be put in and taken out sideways and a tube carrier device for putting in and taking out the tube can be simplified.

In this coupled tester, however, a tube transfer mechanism between the tube carrier device for carrying the tested tube into and out of the test line between both the stocks and a tube clamping device for fixing the tested tube to the test line between both the stocks is inevitably complicated. In other words, when the tube carrier device carries the tested tube into the test line between both the stocks sideways, a tube support portion of the tube clamping device needs to be in a sufficiently lower position than a home position in the test line so as to avoid interference with the tested tube and the tube support portion needs to lift after the carry in to lift the tested tube to the test line. As a result, lifting and lowering strokes of the tube support portion become large to cause a problem of increase in size of the tube clamping device.

In addition, in the tube clamping device, clamp claws on opposite sides obstruct the carry in of the tube unless the clamp claws are fully opened to the opposite sides. Here, as the tube clamping device, a device having clamp claws which are opened and closed by utilizing lifting and lowering operations is preferable because of its simple structure (Patent Document 1). However, in such a tube clamping device, lifting and lowering strokes for opening and closing the clamp claws become large when the clamp claws on the opposite sides are fully opened and, as a result, the tube clamping device inevitably increases in size.

PRIOR ART DOCUMENT

Patent Document

[Patent Document 1] JP 2001-88924 A

DISCLOSURE OF THE INVENTION

Problems to be Solved by the Invention

It is an object of the present invention to provide a compact tube clamping device with a simple structure, in which increase in height of the device due to lifting and lowering operations can be minimized, while the device can transfer a tube by the lifting and lowering operations and clamping claws on opposite sides are opened and closed by utilizing the lifting and lowering operations.

It is another object of the invention to provide a compact hydraulic pressure tester with a simple structure and using the compact tube clamping devices with the simple structures.

Means for Solving the Problems

To achieve the object, a tube clamping device according to the present invention includes a fixed base installed on a tube treatment line; a lifting/lowering base provided onto the fixed base to be able to lift and lower and including a tube support body for supporting and centering a tube on itself; a first drive mechanism mounted to the fixed base so as to drive the lifting/lowering base for lifting and lowering; paired opposite clamp claws mounted in positions, between which the tube support body of the lifting/lowering base is sandwiched, to be able to turn so as to clamp the tube supported on the tube support body; a lifting/lowering claw drive body provided in the lifting/lowering base so as to lift and lower independently of the lifting/lowering base and having opposite side portions connected to the opposite clamp claws by links so as to turn the clamp claws on opposite sides of the lifting/lowering base in closing directions by lowering with respect to the lifting/lowering base; and a second drive mechanism mounted to the fixed base so as to drive the claw drive body for lifting and lowering.

In the tube clamping device according to the invention, it is possible to transfer the tube by lifting and lowering of the tube support body mounted to the lifting/lowering base on the fixed base. In other words, by driving of the lifting/lowering base by the first drive mechanism, the tube is carried into the position on the tube support body when the tube support body has lowered. The tube support body lifts in this state, so that it supports the tube on itself. At this time, as a result of the lifting of the lifting/lowering base for lifting the tube support body, the lifting/lowering claw drive body lowers with respect to the lifting/lowering base. In this way, the opposite clamp claws mounted to the opposite sides of the lifting/lowering base close into a half open state. The claw drive body is further driven for lowering by the second drive mechanism from this state, so that the opposite clamp claws shift into a fully open state to grasp and fix the tube on the tube support body irrespective of a diameter of the tube.

In other words, the opposite clamp claws are closed to the half open state by utilizing the lifting of the lifting/lowering base including the tube support body necessary for the transfer of the tube and then, the remaining closing operation is carried out by lowering of the claw drive body. In this way, a lowering stroke of the claw drive body necessary for closing operations of the clamp claws is partially born by the lifting of the lifting/lowering base in transferring the tube. Therefore, the lowering stroke of the claw drive body for opening and closing the clamp claws can be suppressed.

In the tube clamping device of the present invention, preferably, the opposite clamp claws fully open with the lifting/lowering base being positioned at a lowering limit and the claw drive body being positioned at a lifting limit and the opposite clamp claws are positioned at the same level as the tube support body between the clamp claws in the fully open state. This structure prevents the clamp claws from obstructing handing and receiving of the tube to and from the tube support body. As a result, the clamp claws open wide in a standby state and turning operations in closing are large. However, increase in the lowering stroke of the claw drive body resulting from this can be suppressed as described above.

That is, the lifting/lowering base is driven from the lowering limit to a lifting limit with the claw drive body being positioned at the lifting limit, so that the claw drive body lowers with respect to the lifting/lowering base to drive the opposite clamp claws for turning into a half open state. Then the claw drive body lowers from the lifting limit with the lifting/lowering base being driven from the lowering limit to the lifting limit, so that the opposite clamp claws further close to clamp the tube on the tube support body irrespective of a tube diameter.

A hydraulic pressure tester of the present invention is the hydraulic pressure tester for pinching a manufactured tube between a head stock, for sealing a tube end and injecting and discharging high-pressure water, and a tail stock, for sealing a tube end, and injecting the high-pressure water into the tube, wherein the tube clamping devices according to the present invention are arranged, as tube support mechanisms between the head stock and the tail stock, in a longitudinal direction between both the stocks.

Because the tube clamping devices arranged in the longitudinal direction between both the stocks are compact and have simple structures in the hydraulic pressure tester according to the invention, the tester itself is compact and lightweight and has a simple structure.

Especially, by connecting support bodies of both the stocks with an upper beam and a lower beam so that opposite sides of the tube support line between the head stock and the tail stock are open, the tester is further made compact and lightweight. By connecting the support bodies of both the stocks with the upper beam and the lower beam, handing and receiving of the tube from the open sides are carried out smoothly.

Specifically, horizontal tube support beams orthogonal to the tube support line between the head stock and the tail stock and for sliding in the orthogonal direction are disposed in a plurality of positions between both the stocks so as not to interfere with the tube clamping devices between both the stocks, a tube support level by the plurality of tube support beams is higher than a tube support level by the tube support bodies of the tube clamping devices, and each of the tube support bodies moves from the lowering limit to the lifting limit together with the lifting/lowering base, so that the tube support level by the tube support bodies of the tube clamping devices becomes higher than the tube support level by the plurality of tube support beams. In this way, handing and receiving of the tube to and from the tube support line between both the stocks from the open sides are carried out smoothly by the support beams.

Preferably, each of the tube support beams has tube support bodies for supporting and centering the tube on themselves in at least two positions in a longitudinal direction (a direction of sliding). With this structure, a standby line can be set on one of outer sides of the tube support line between both the stocks and a drain line for discharging remaining water can be set on the other outer side. While the hydraulic pressure test is carried out on the tube support line between both the stocks, carry of the tube into the standby line and discharge of the water remaining in the tube on the drain line can be carried out simultaneously.

Although both the head stock and the tail stock are normally movable in a front-back direction of the tube support line for insertion and fixing of tube end portions and to conform to change in tube length, a structure in which the head stock for carrying out injection and discharge of the high-pressure water is fixed and only the tail stock is movable in the front-back direction is preferable. With this structure, pipes such as a high-pressure pipe and a low-pressure pipe attached to the head stock are fixed and risk of leakage of the high-pressure water is reduced.

In this case, the tail stock includes a detecting mechanism for a tube end, on a side of the tail stock, of the tube on standby beside the tube support line between both the stocks and is guided in advance to a moving position corresponding to a detected tube end position. In this way, operation for conforming to the change in the tube length is carried out swiftly and time required for the test can be shortened.

As the arrangement of the tube clamping device between the stocks, the tube clamping device is fixedly installed behind the head stock, the tube clamping device is provided to be movable with the tail stock in front of the tail stock, and one or the plurality of tube clamping device(s) is (are) disposed between the fixed tube clamping device on the side of the head stock and the movable tube clamping device on the side of the tail stock.

With such an arrangement, preferably at least one tube clamping device on the side of the tail stock out of the one or the plurality of tube clamping device(s) disposed between the fixed tube clamping device on the side of the head stock and the movable tube clamping device on the side of the tail stock can tilt to a receding position so as not to obstruct forward movement of a movable portion on the side of the tail stock. In other words, with only the tail stock being movable in the front-back direction, a movement stroke of the tail stock is necessarily long in order to conform to the change in the tube length only with the movement of the tail stock. On the other hand, it is essential to dispose the one or the plurality of tube clamping device(s) between the fixed tube clamping device on the side of the head stock and the movable tube clamping device on the side of the tail stock in order to reliably fix a long tube. As a result, there is a fear that the tube clamping device disposed between the fixed tube clamping device on the side of the head stock and the movable tube clamping device on the side of the tail stock obstructs forward movement of the movable portion on the side of the tail stock. However, if at least one tube clamping device on the side of the tail stock out of the one or the plurality of tube clamping device(s) disposed between the fixed tube clamping device on the side of the head stock and the movable tube clamping device on the side of the tail stock can tilt to such a receding position as not to obstruct the forward movement of the movable portion on the side of the tail stock, it is possible to adapt to a large change in the tube length while reliably fixing the long tube.

Effect of the Invention

In the tube clamping device according to the invention, the lowering stroke of the claw drive body necessary for the closing operations of the clamp claws is partially born by the lifting of the lifting/lowering base in transferring the tube and therefore the lowering stroke of the claw drive body for opening and closing the clamp claws can be suppressed. As a result, the height of the tube clamping device can be suppressed. The clamp claws open wide to the opposite sides, which makes handing and receiving of the tube to and from the tube support body easy and suppresses the lifting stroke of the lifting/lowering base to thereby suppress height of the tube clamping device. As described above, even if the clamp claws open wide to the opposite sides, the lowering stroke of the claw drive body required for the closing operation can be suppressed and increase in size of the tube clamping device can be avoided.

Because the compact tube clamping devices having the simple structures are arranged in the longitudinal direction between the head stock and the tail stock as tube support mechanisms between both the stocks, the hydraulic pressure tester according to the invention is compact and lightweight and has the simple structure.

BRIEF DESCRIPTIONS OF THE DRAWINGS

Figure 3:
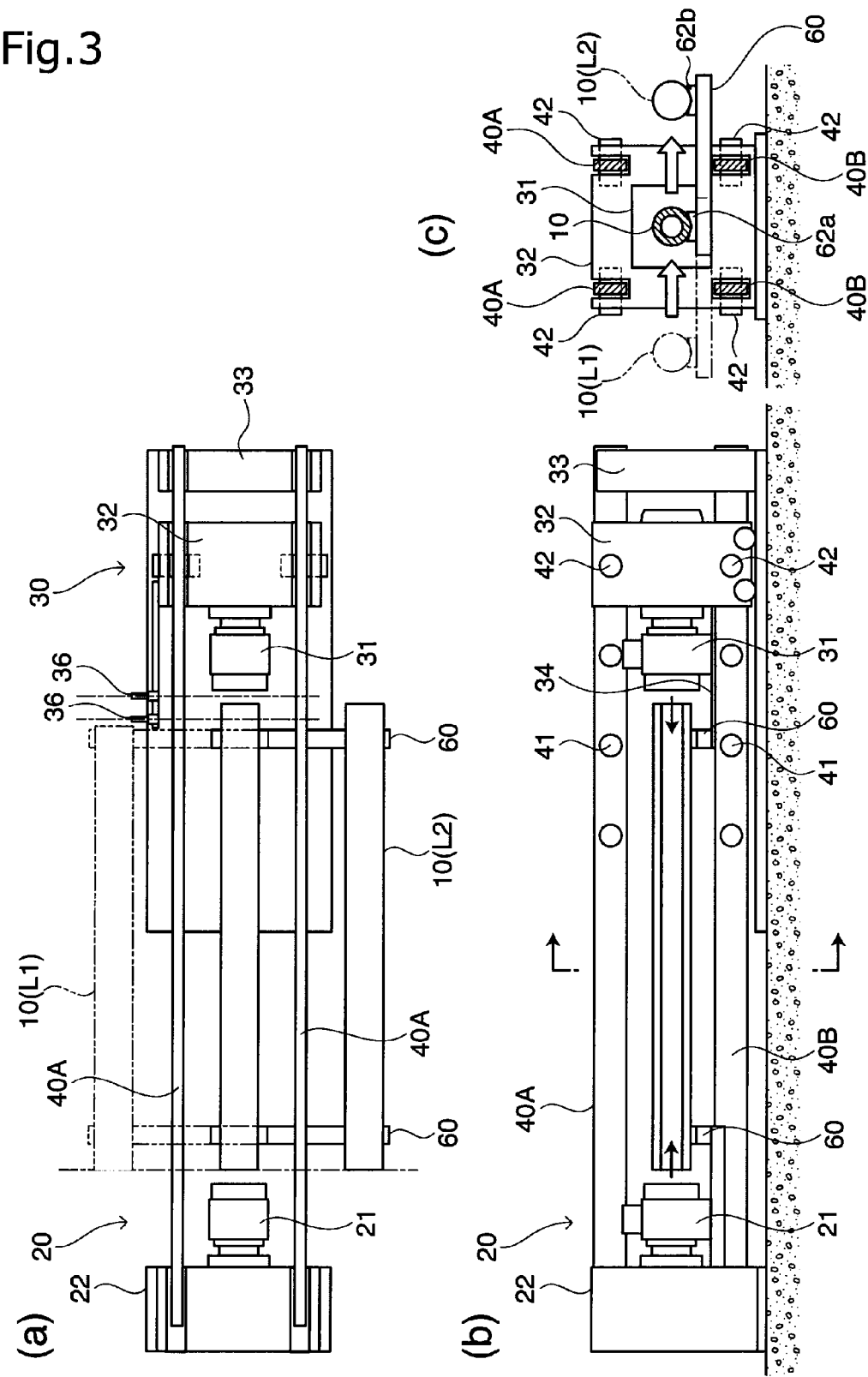

FIGS. 3(a) to 3(c) are schematic three orthogonal views of the hydraulic pressure tester, wherein FIG. 3(a) is a plan view, FIG. 3 (b) is a side view, and FIG. 3(c) is a sectional view taken in a direction of arrows along line A-A in FIG. 3(a).

Figure 4:
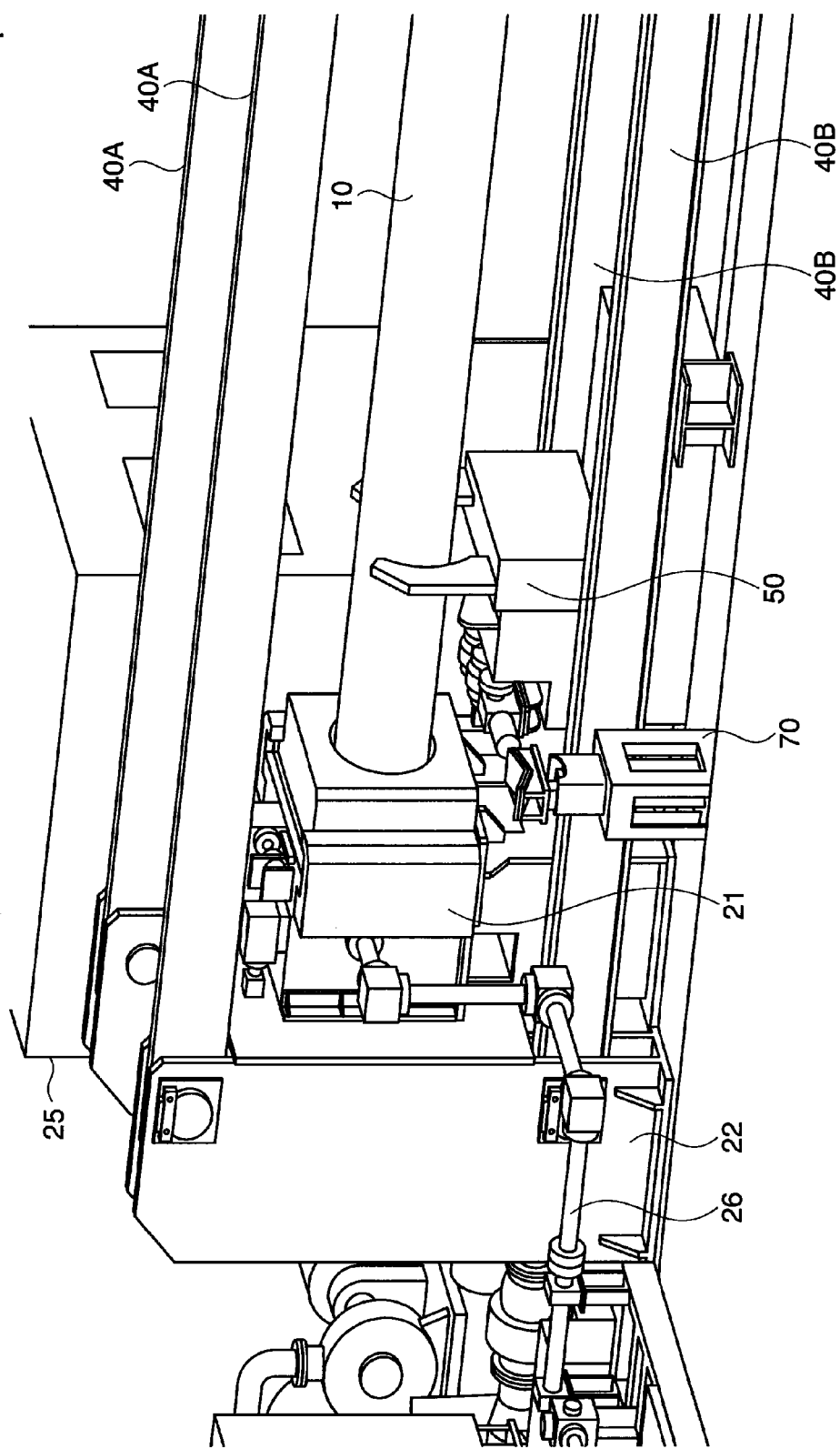

FIG. 4 is a perspective view of a vicinity of a head stock of the hydraulic pressure tester.

Figure 5:
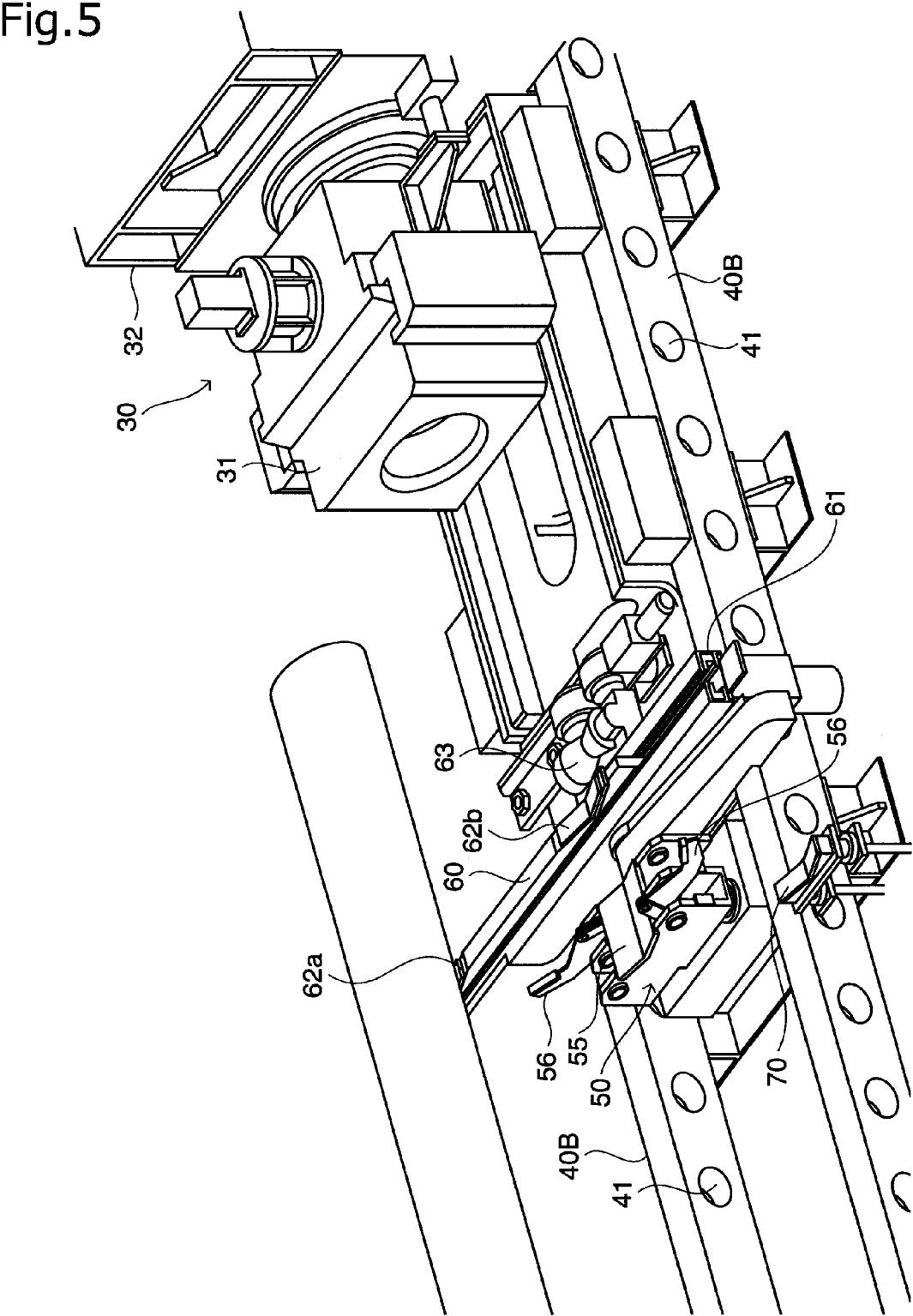

FIG. 5 is a perspective view of a vicinity of a tail stock of the hydraulic pressure tester.

Figure 6:
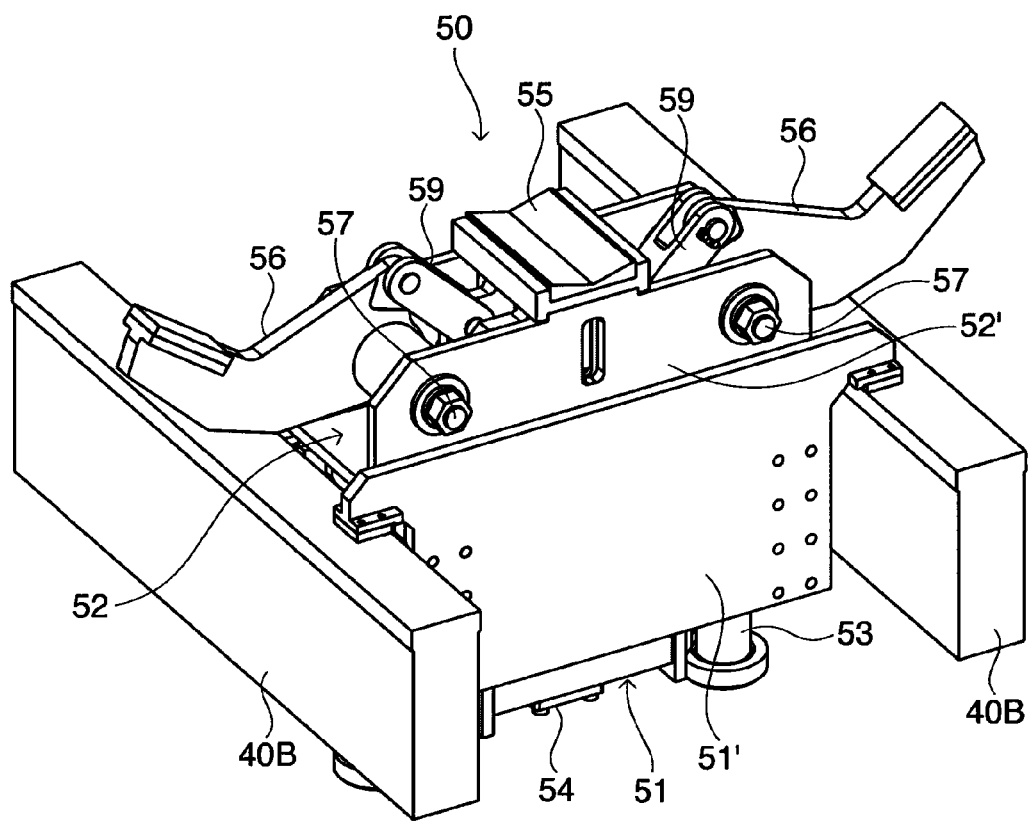

FIG. 6 is a perspective view of a tube clamping device used for the hydraulic pressure tester from a front side.

Figure 7:
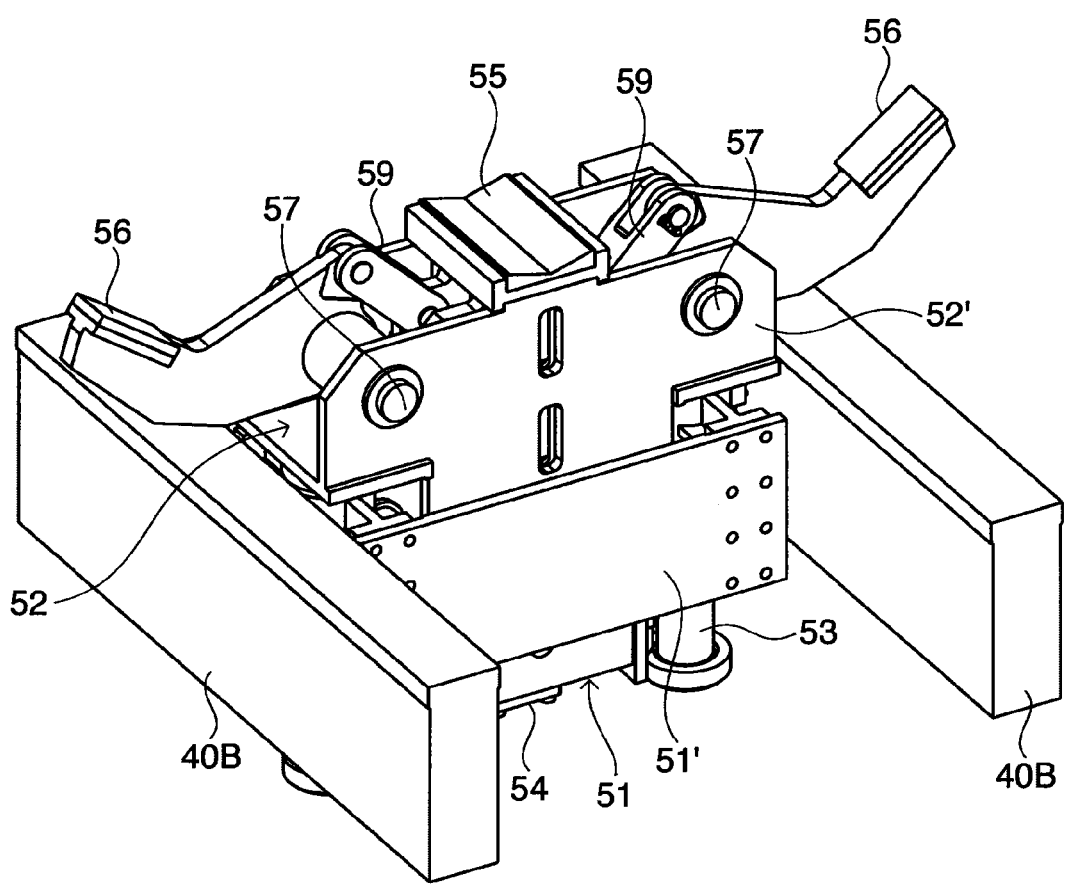

FIG. 7 is a perspective view of the tube clamping device from a rear side.

Figure 8:
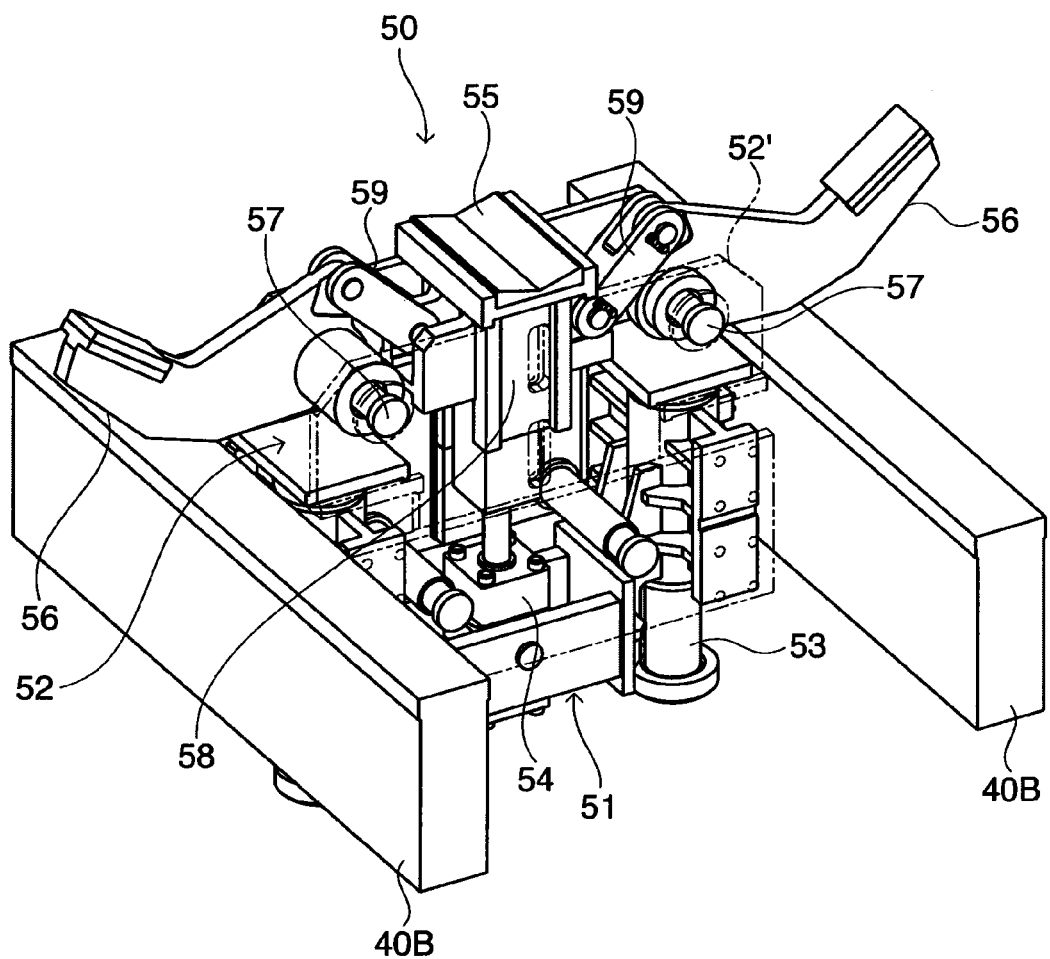

FIG. 8 is a perspective view of an internal structure of the tube clamping device from a rear side.

Figure 9:
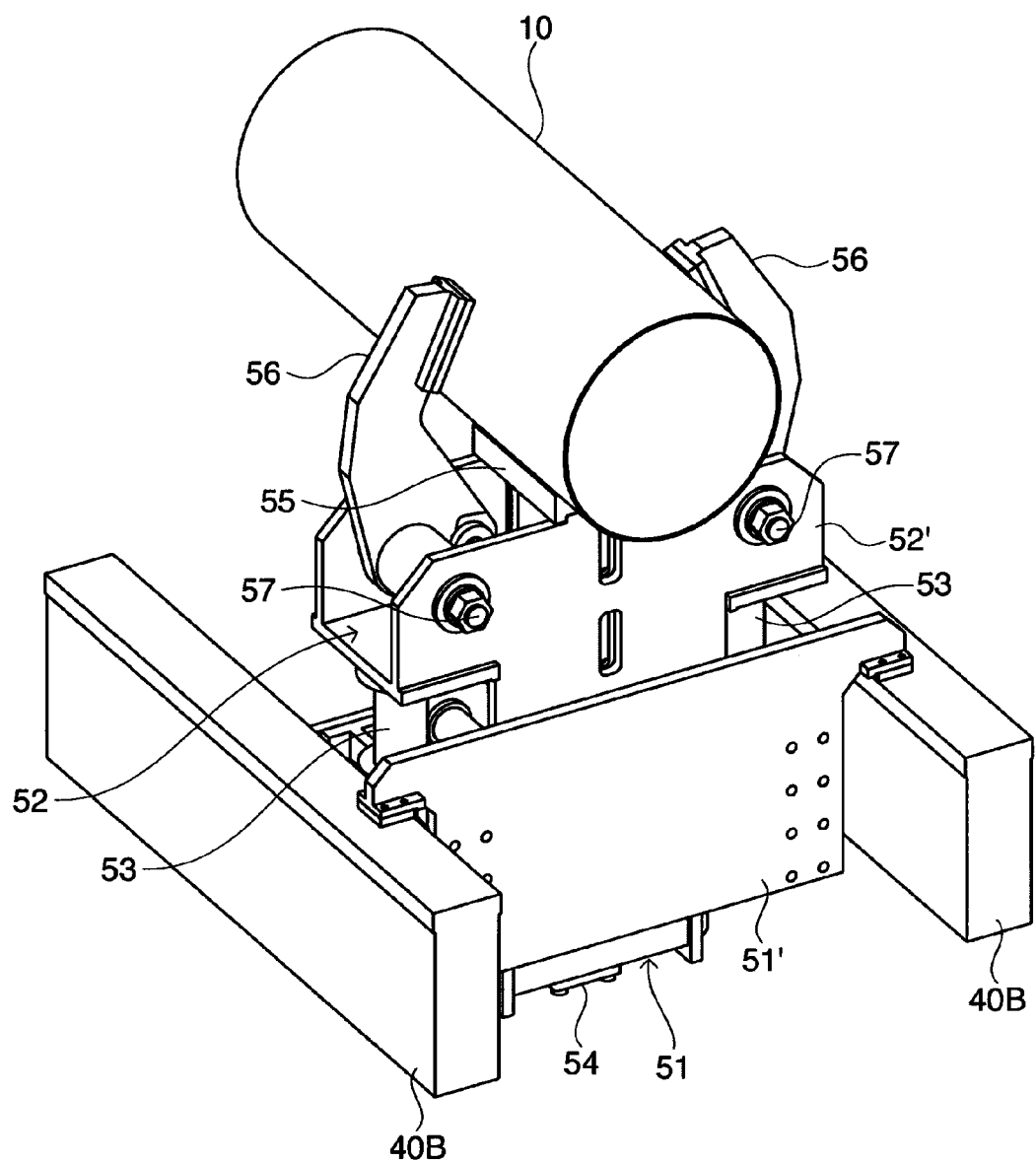

FIG. 9 is a perspective view showing an operating state (clamping state of a large-diameter tube) of the tube clamping device from a front side.

Figure 10:
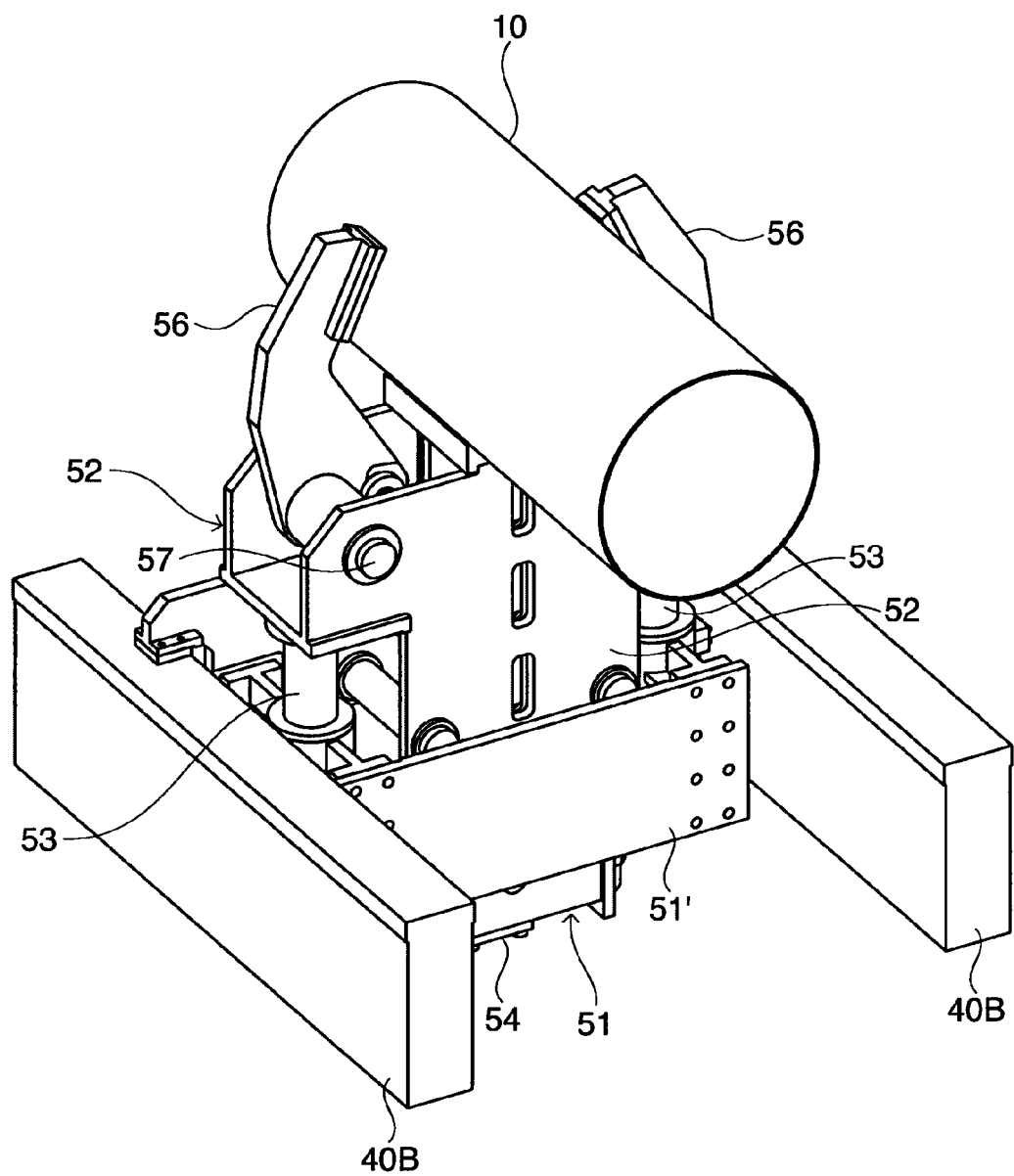

FIG. 10 is a perspective view showing an operating state (clamping state of a large-diameter tube) of the tube clamping device from a rear side.

Figure 11:
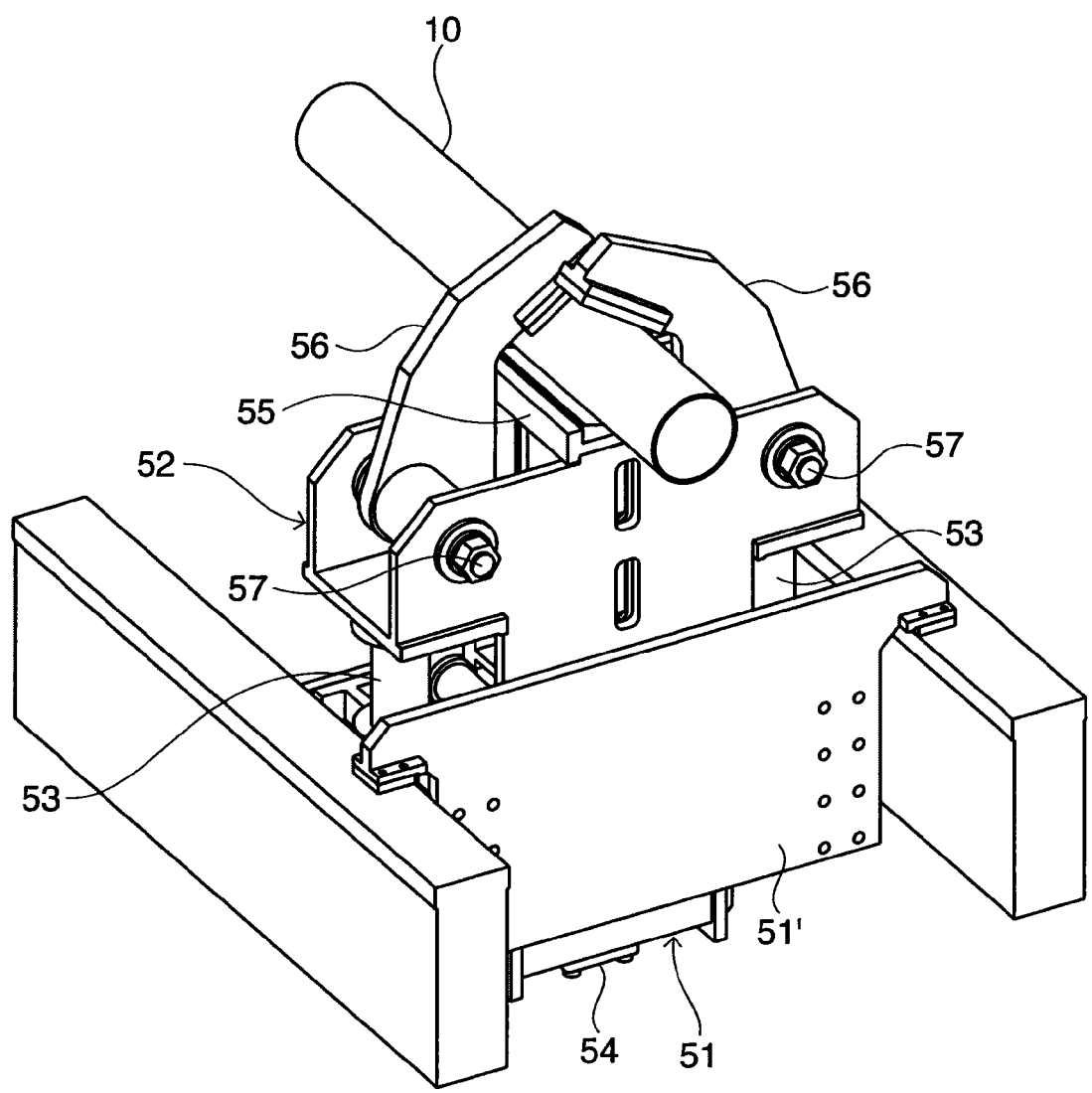

FIG. 11 is a perspective view showing another operating state (clamping state of a small-diameter tube) of the tube clamping device from the front side.

Figure 12:
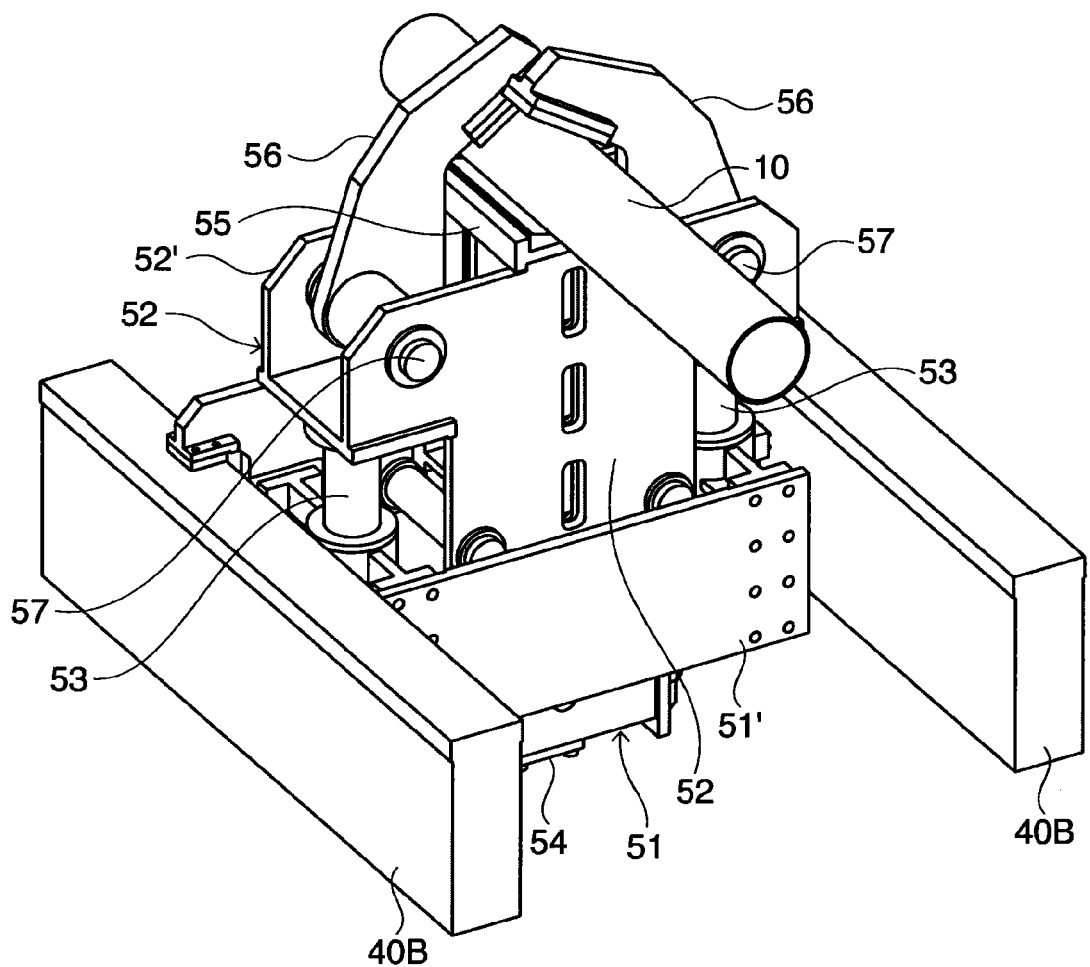

FIG. 12 is a perspective view showing another operating state (clamping state of a small-diameter tube) of the tube clamping device from the rear side.

Figure 13:
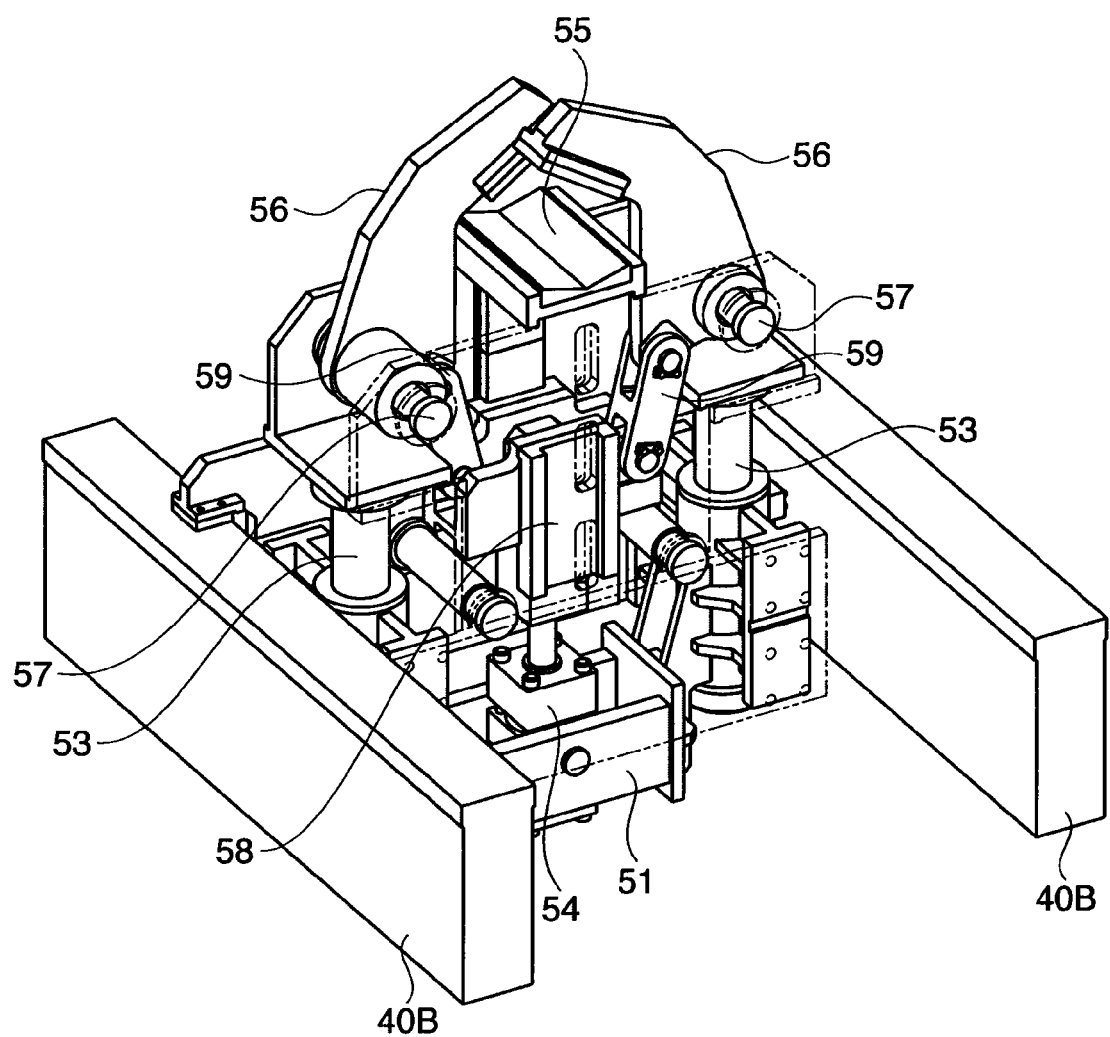

FIG. 13 is a perspective view of the internal structure of the tube clamping device in another operating state (fully closed state).

Figure 14:
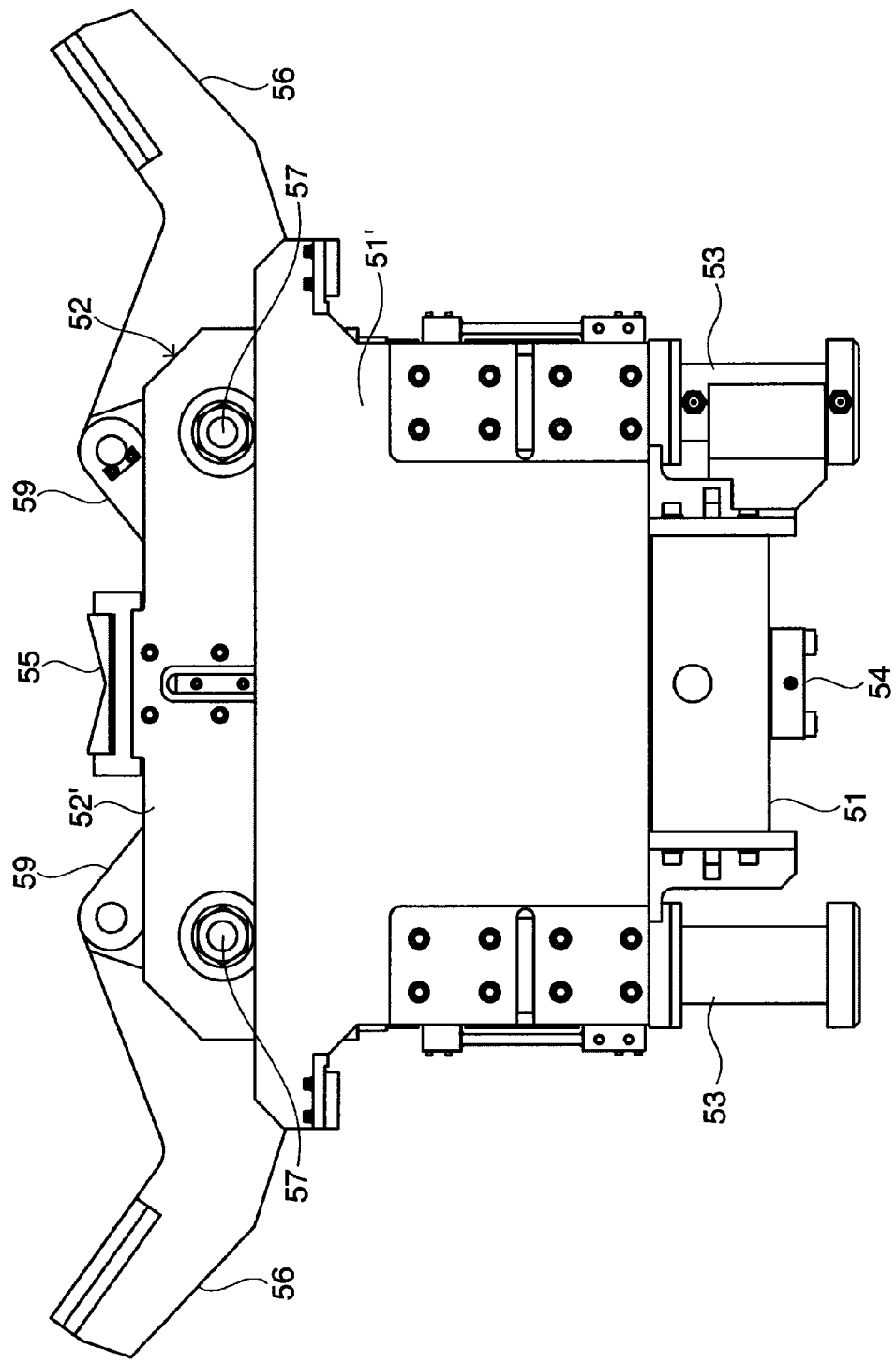

FIG. 14 is a front view of the tube clamping device.

Figure 15:
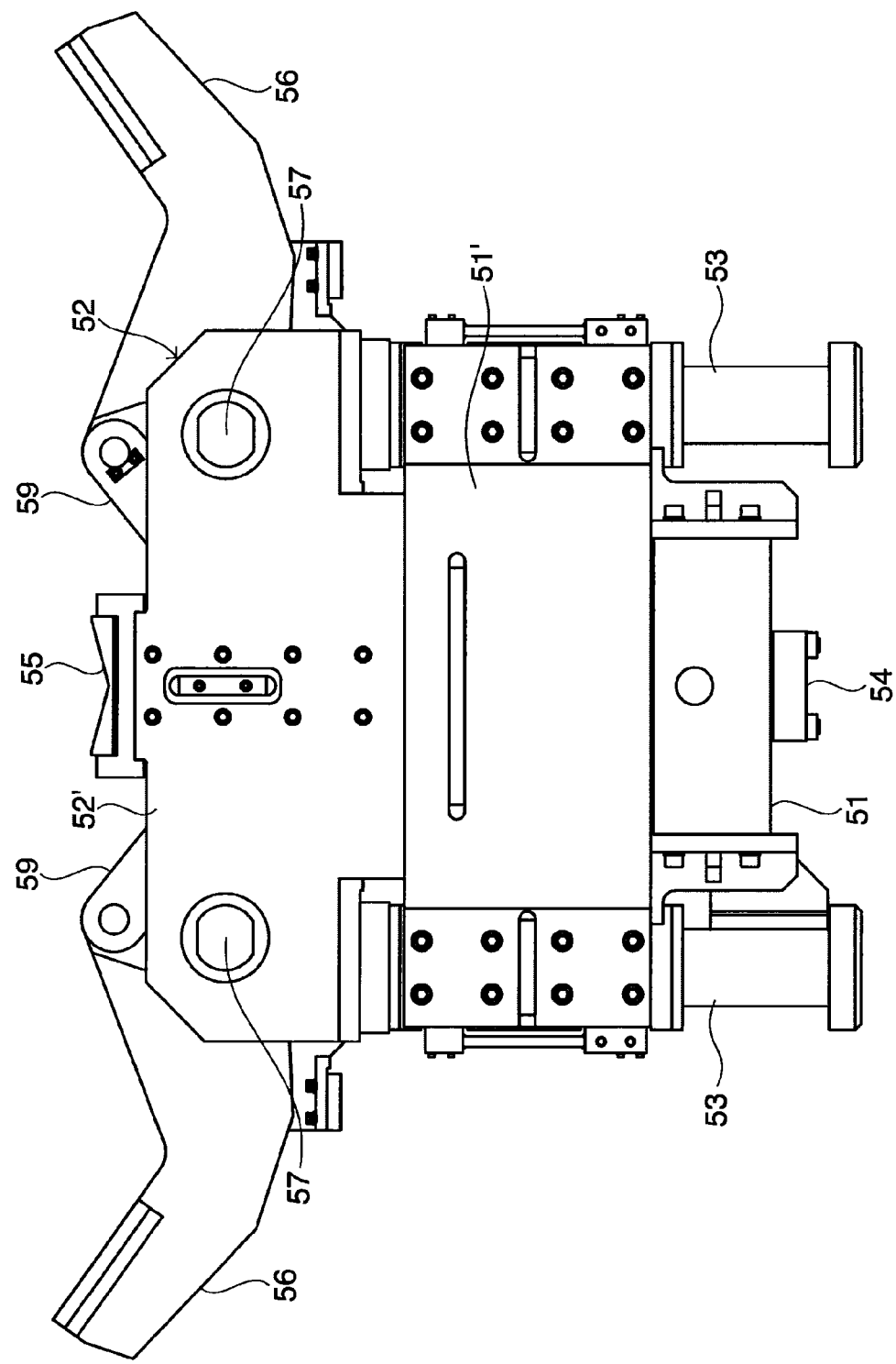

FIG. 15 is a rear view of the tube clamping device.

Figure 16:
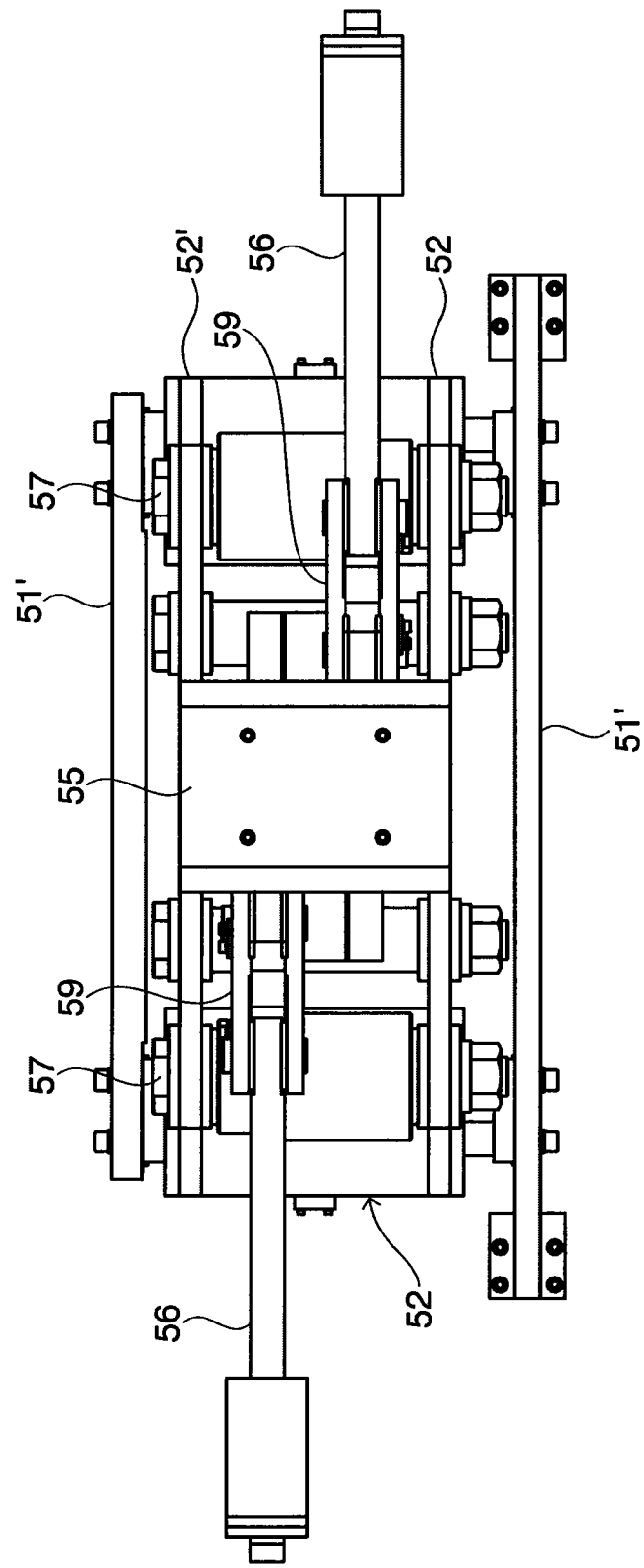

FIG. 16 is a plan view of the tube clamping device.

Figure 17:
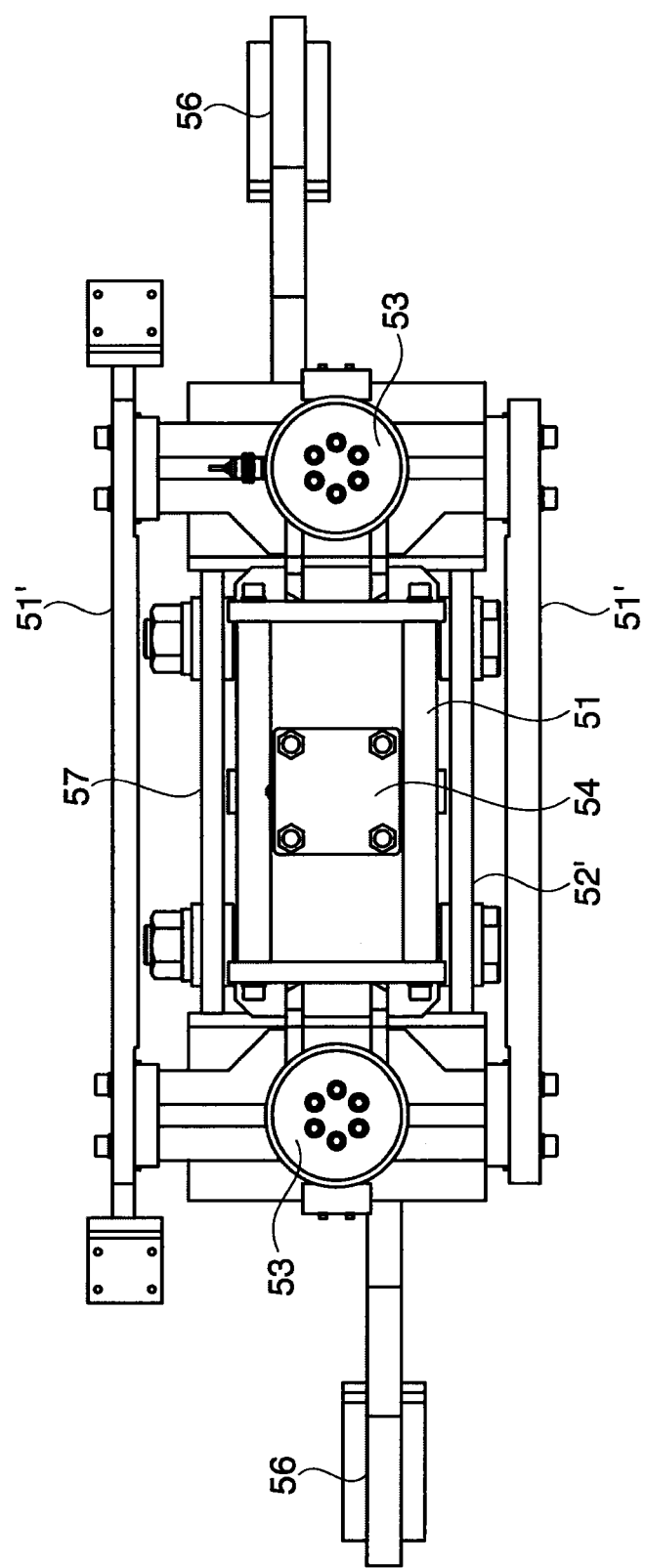

FIG. 17 is a bottom view of the tube clamping device.

Figure 18:
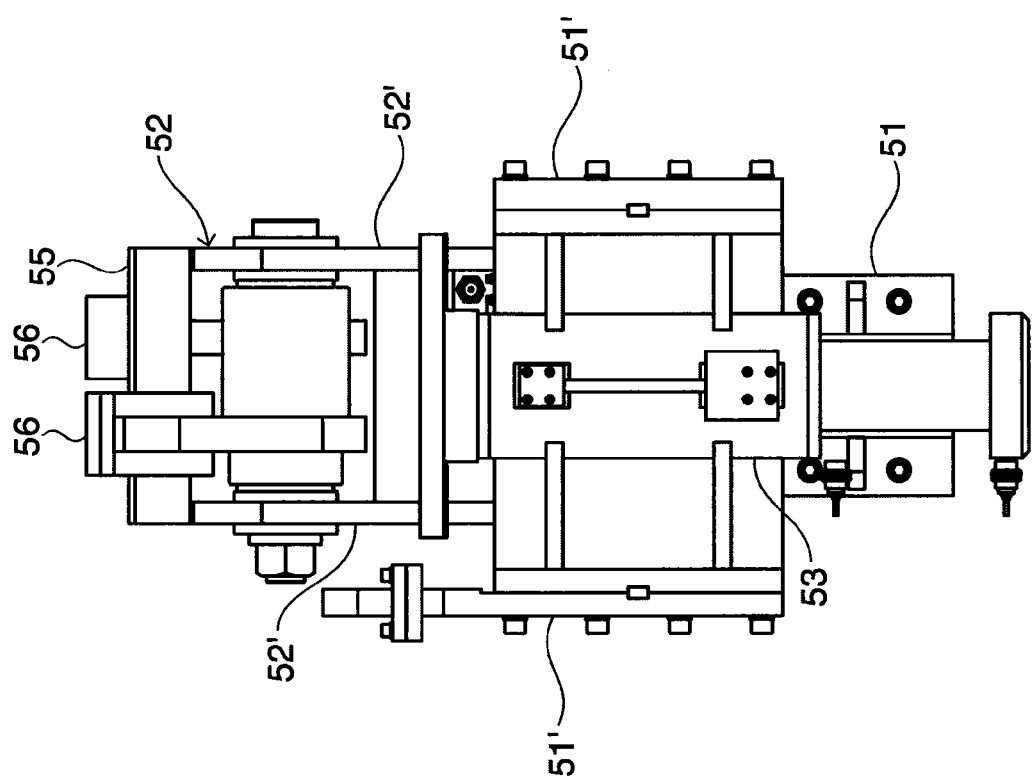

FIG. 18 is a right side view of the tube clamping device.

Figure 19:
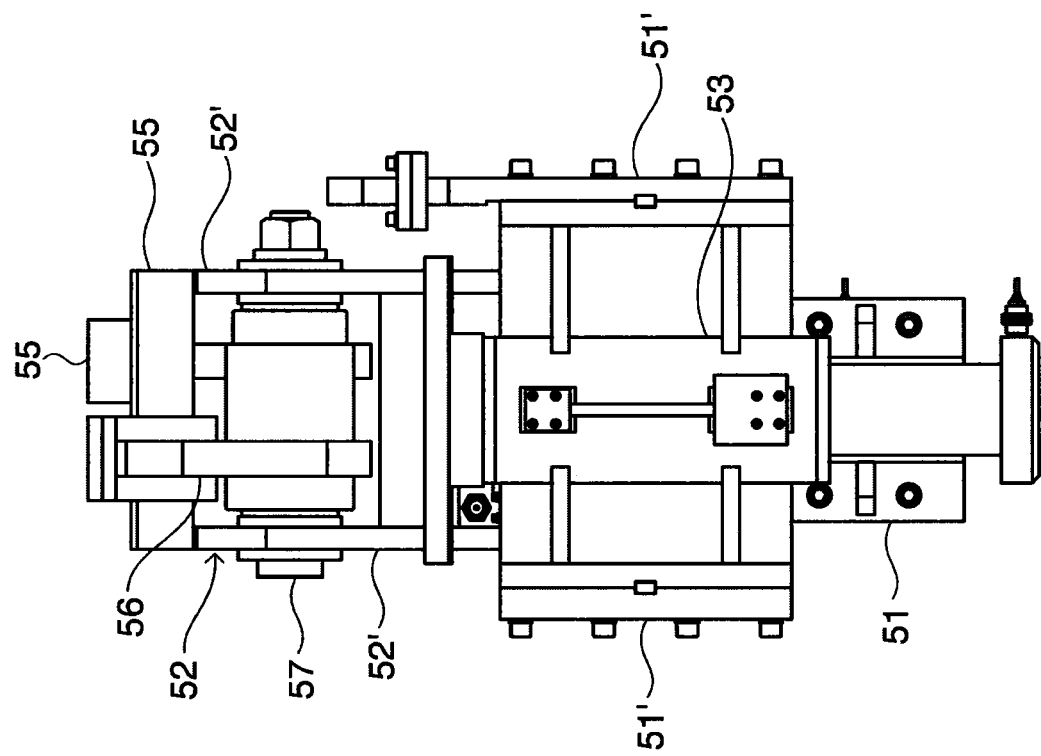

FIG. 19 is a left side view of the tube clamping device.

Figure 20:
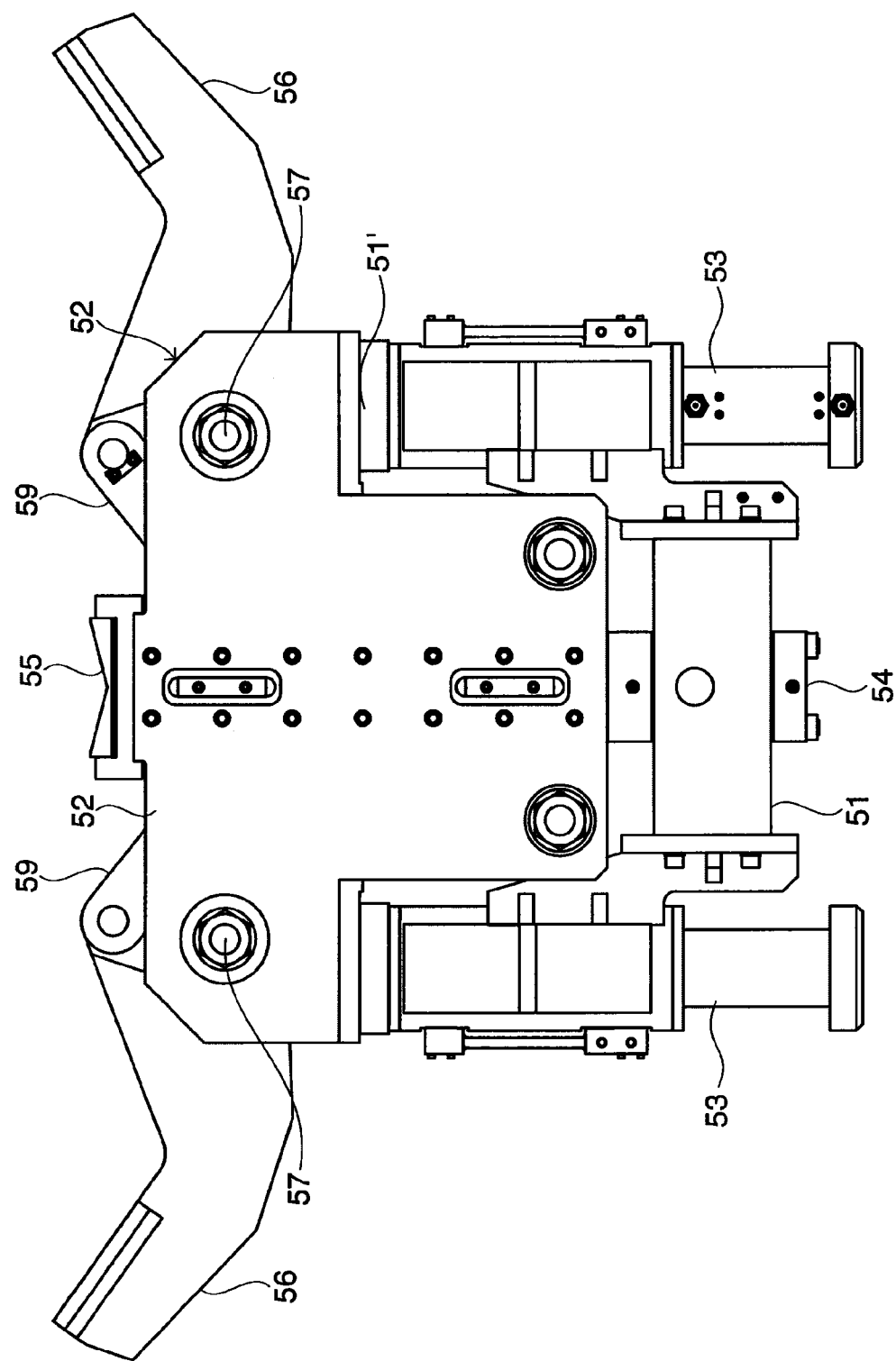

FIG. 20 is a front view of the tube clamping device and showing a state in which reinforcing plates are detached.

Figure 21:
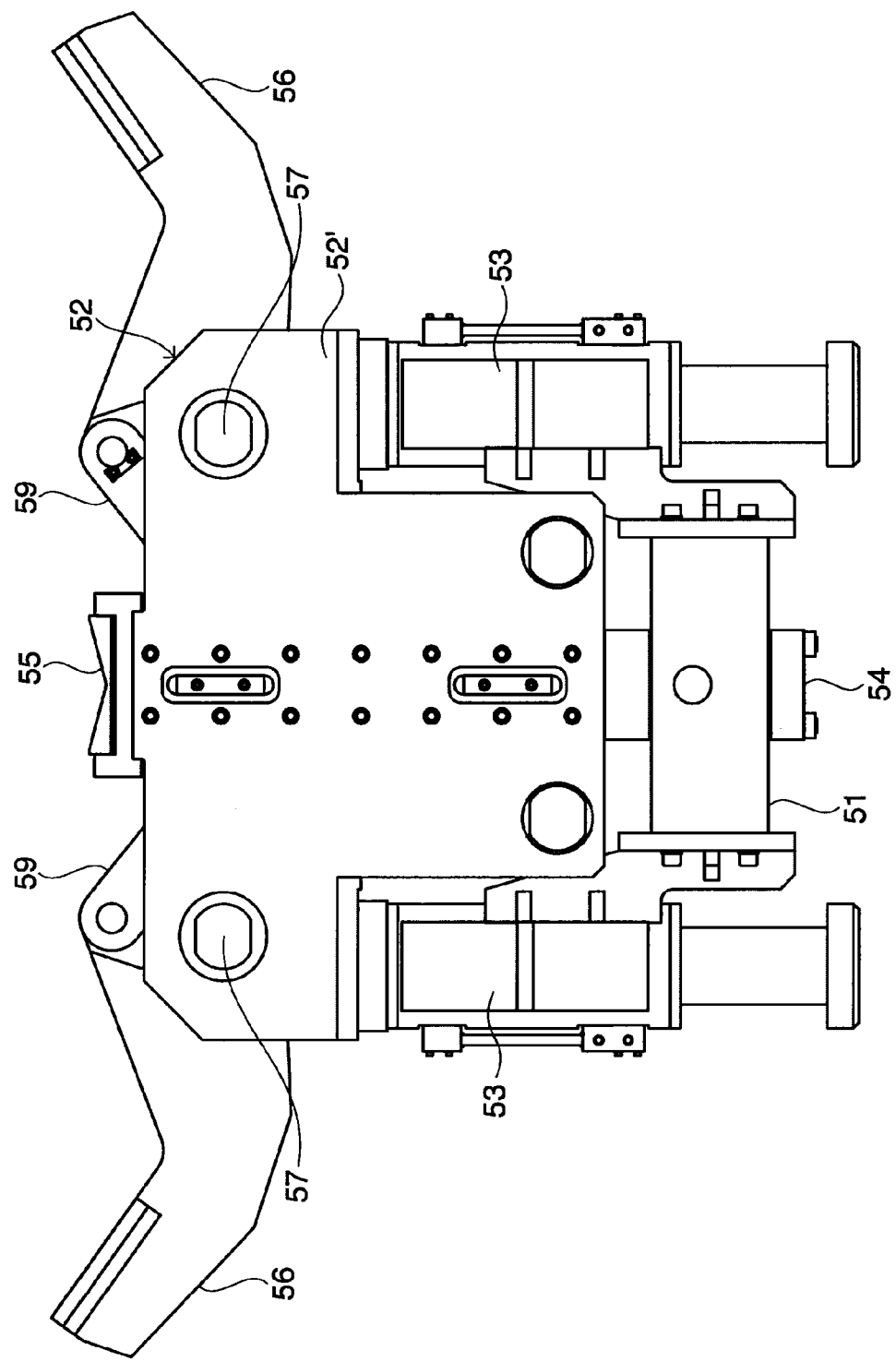

FIG. 21 is a rear view of the tube clamping device and showing a state in which reinforcing plates are detached.

Figure 22:
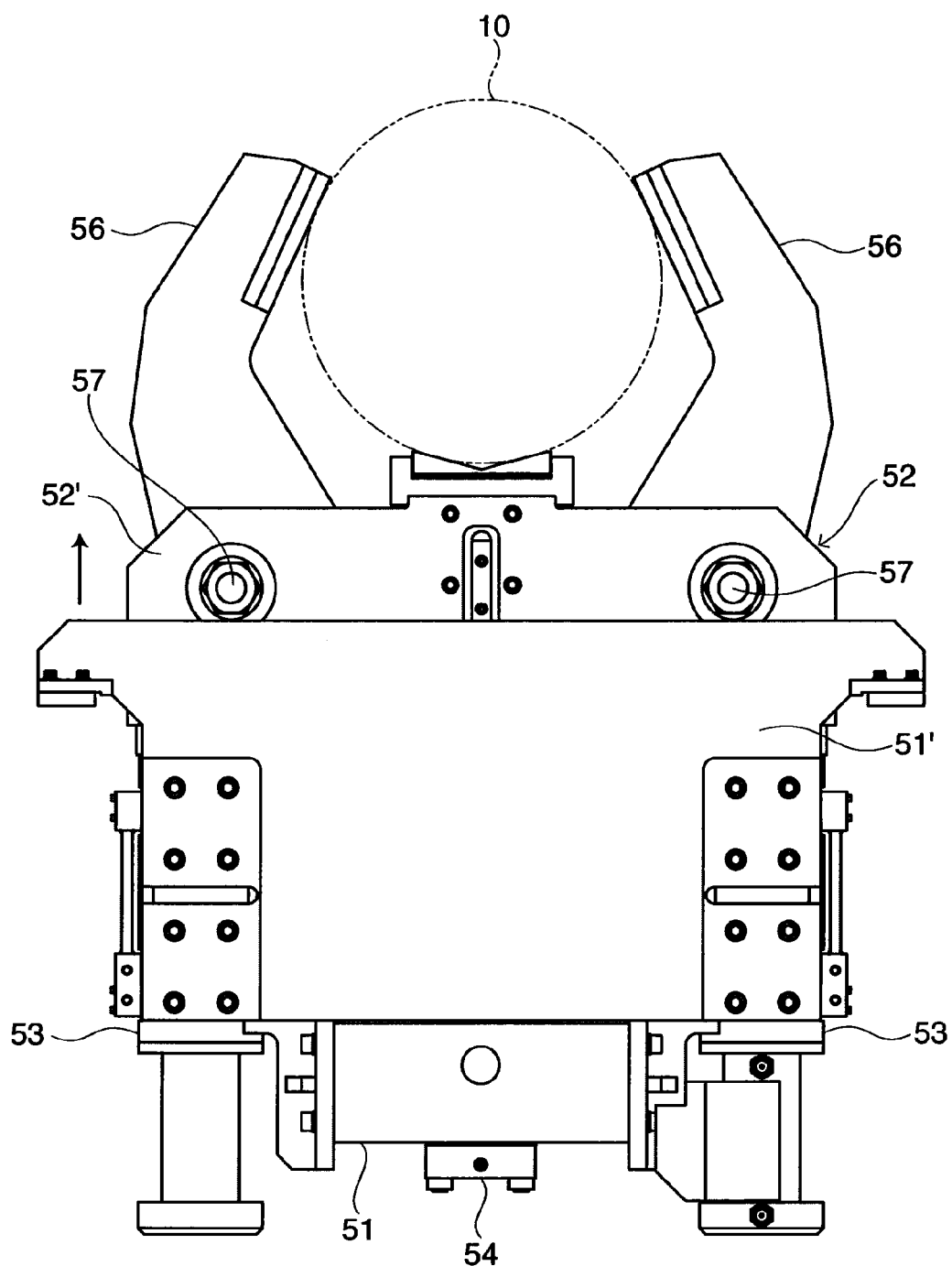

FIG. 22 is a front view of the tube clamping device and showing the operating state (clamping state).

Figure 23:
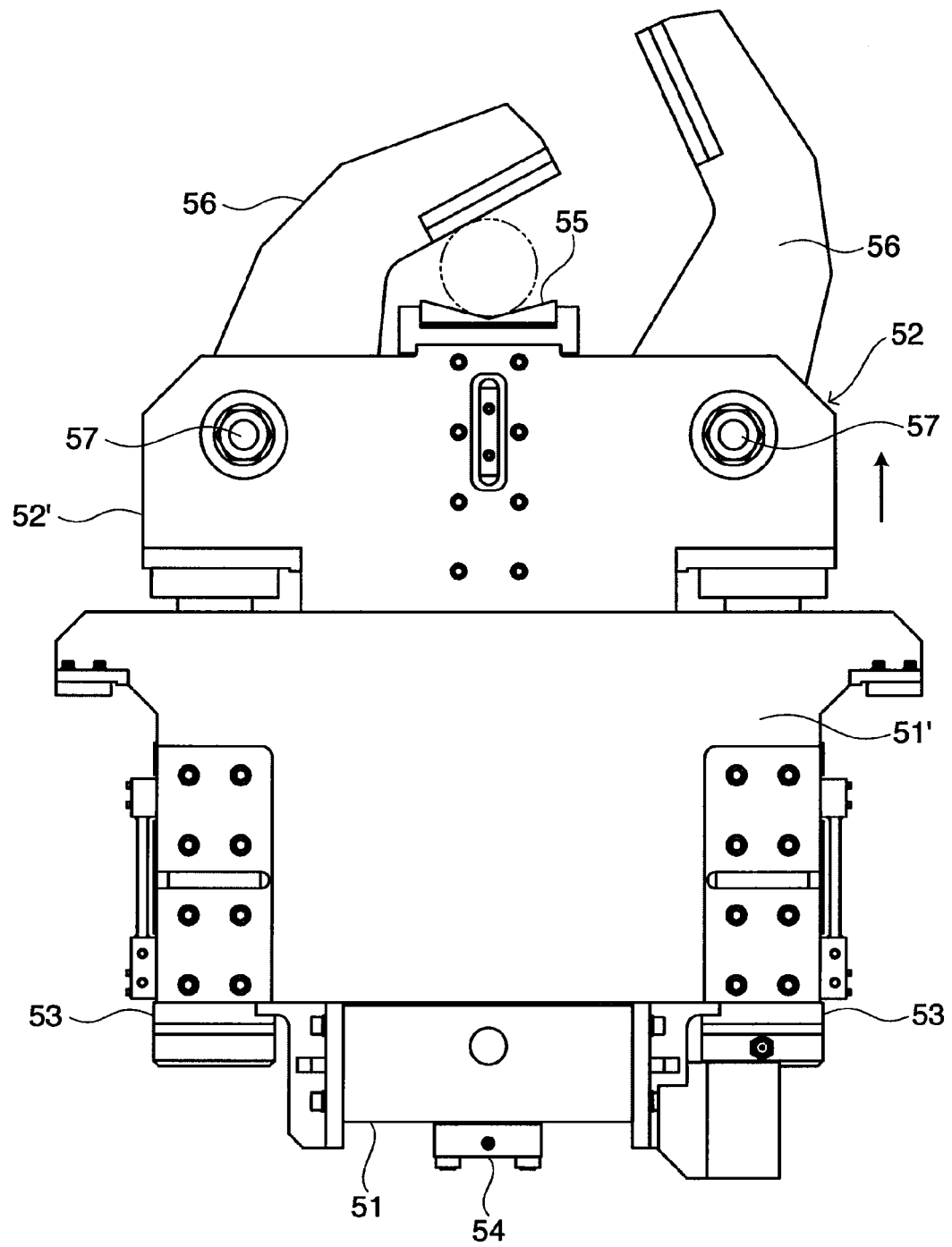

FIG. 23 is a rear view of the tube clamping device and showing the operating state (clamping state).

Figure 24:
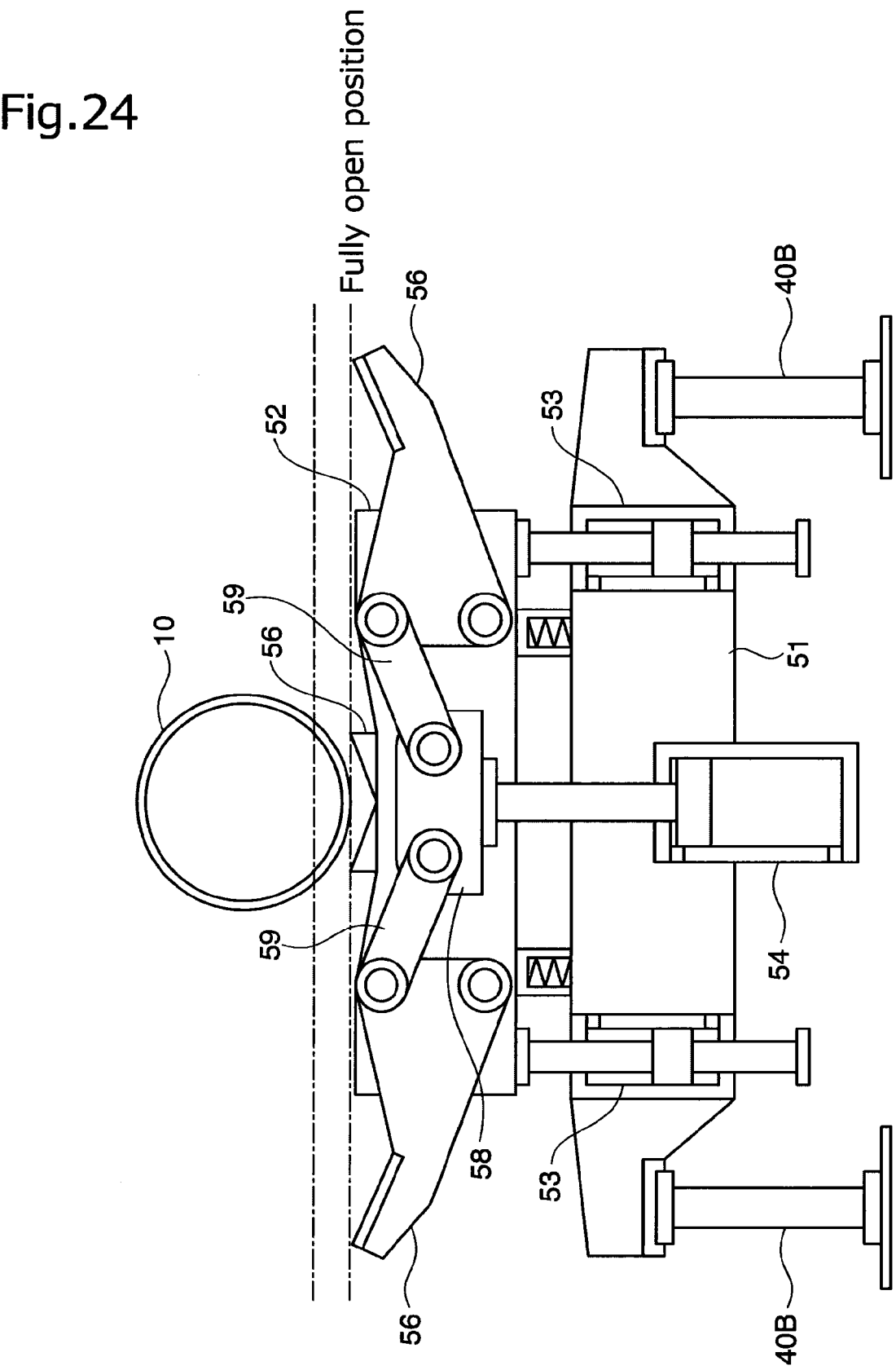

FIG. 24 is a schematic front view showing an operation of the tube clamping device and showing a fully open state.

Figure 25:
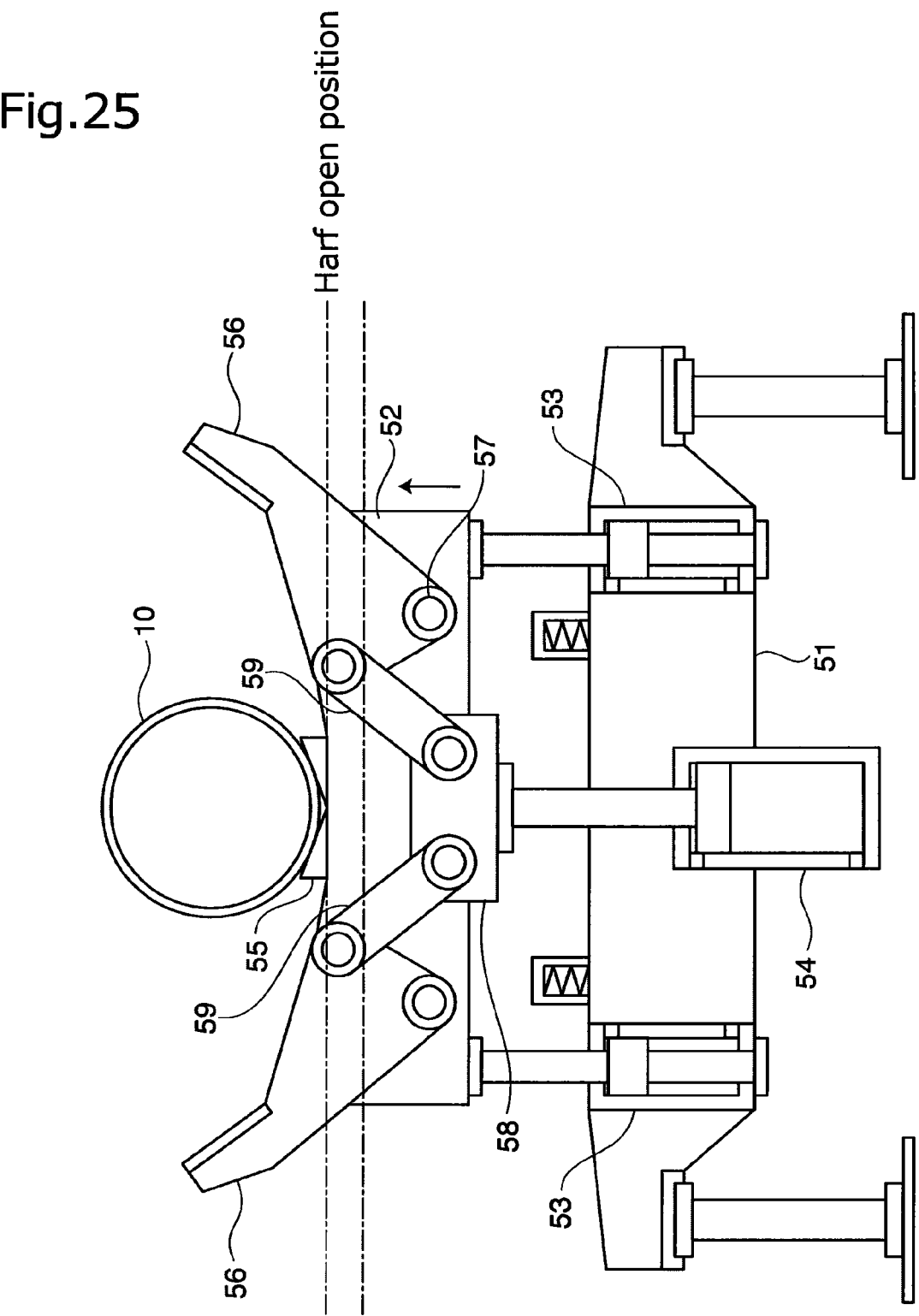

FIG. 25 is a schematic front view showing the operation of the tube clamping device and showing a half open state.

Figure 26:
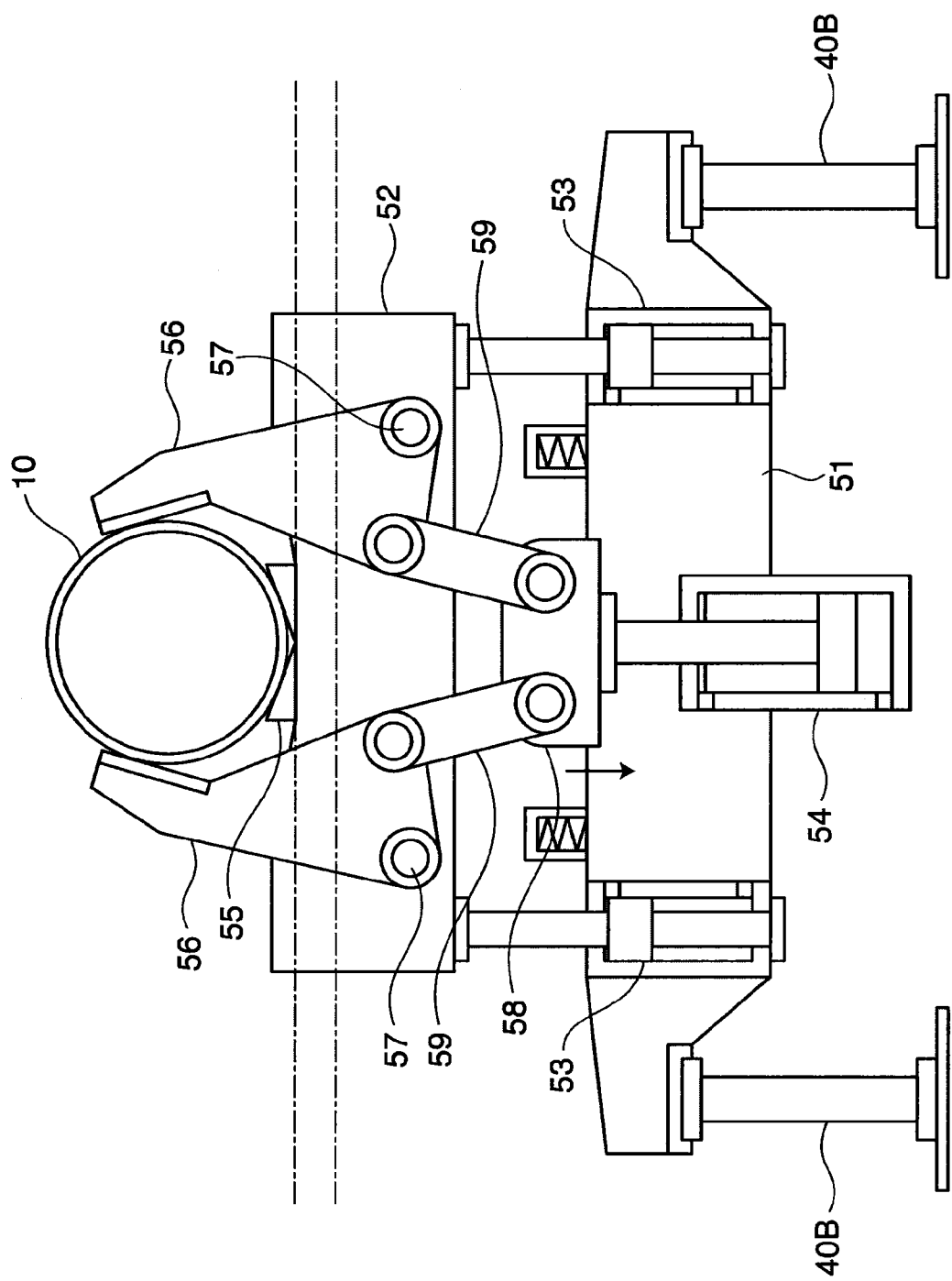

FIG. 26 is a schematic front view showing the operation of the tube clamping device and showing the clamping state of the large-diameter tube.

Figure 27:
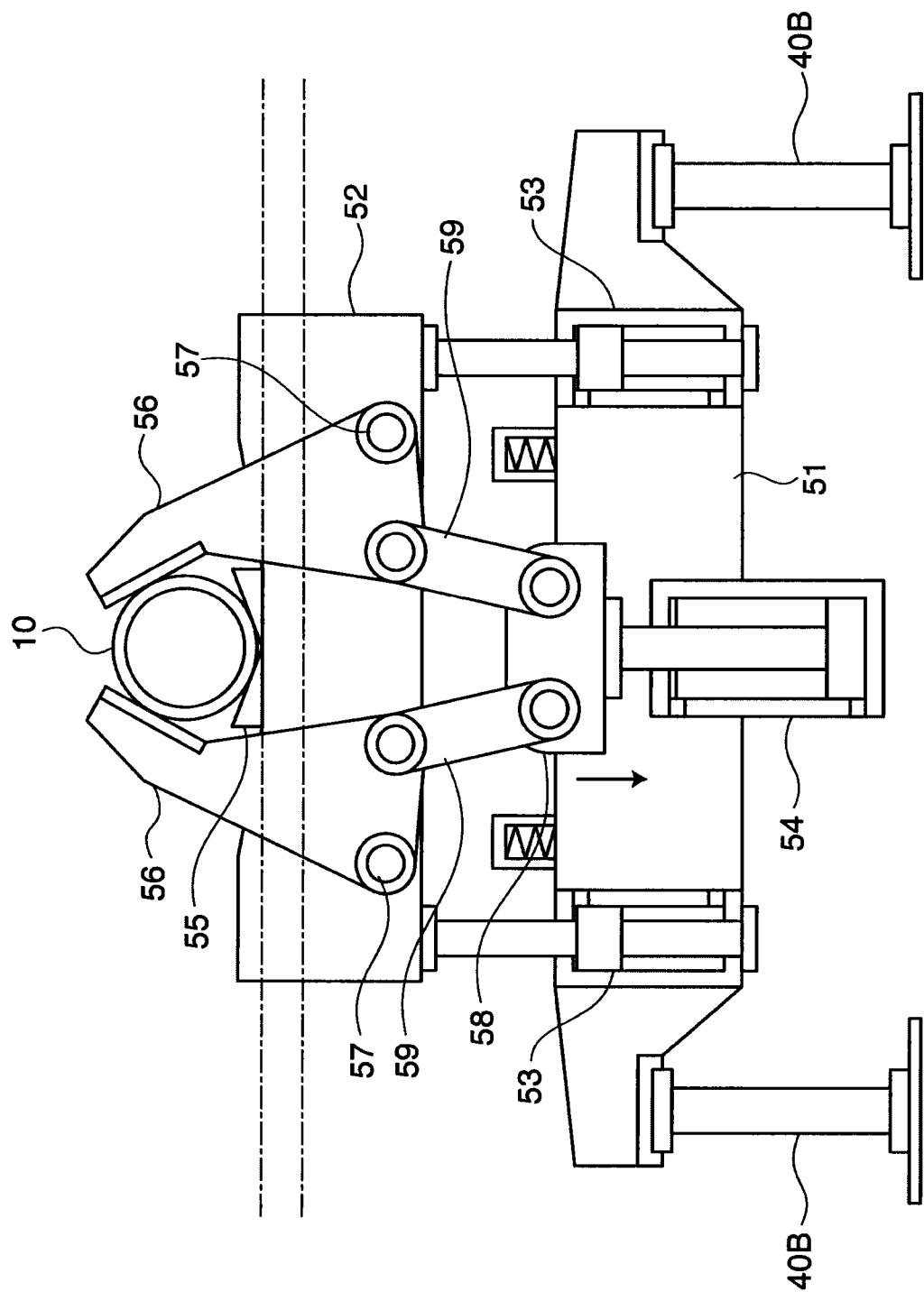

FIG. 27 is a schematic front view showing the operation of the tube clamping device and showing the clamping state of the small-diameter tube.

BEST MODE FOR CARRYING OUT THE INVENTION

An embodiment of the present invention will be described below. A tube clamping device according to the embodiment is used for a hydraulic pressure tester for an electric resistance welded tube manufactured on an electric resistance welded tube manufacturing line.

Figure 1:
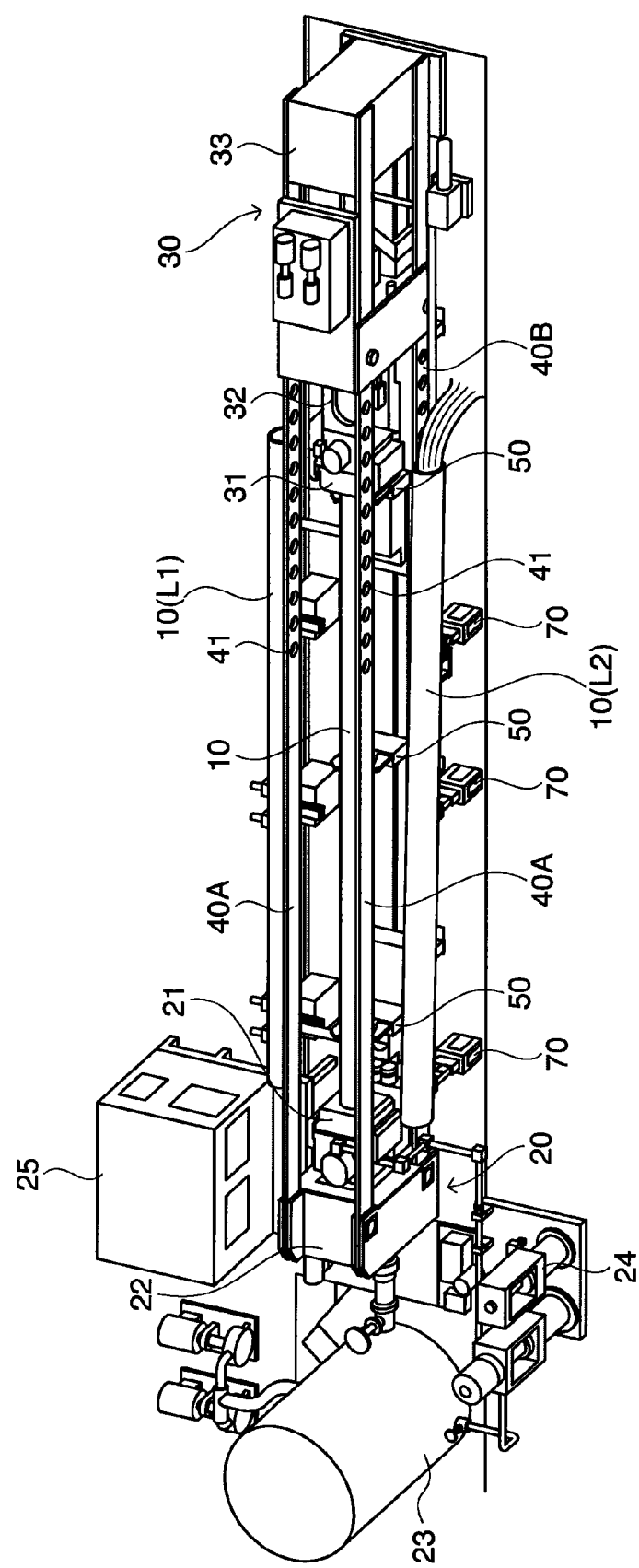
FIG. 1 is a perspective view of a hydraulic pressure tester and showing an embodiment of the present invention.
Figure 2:
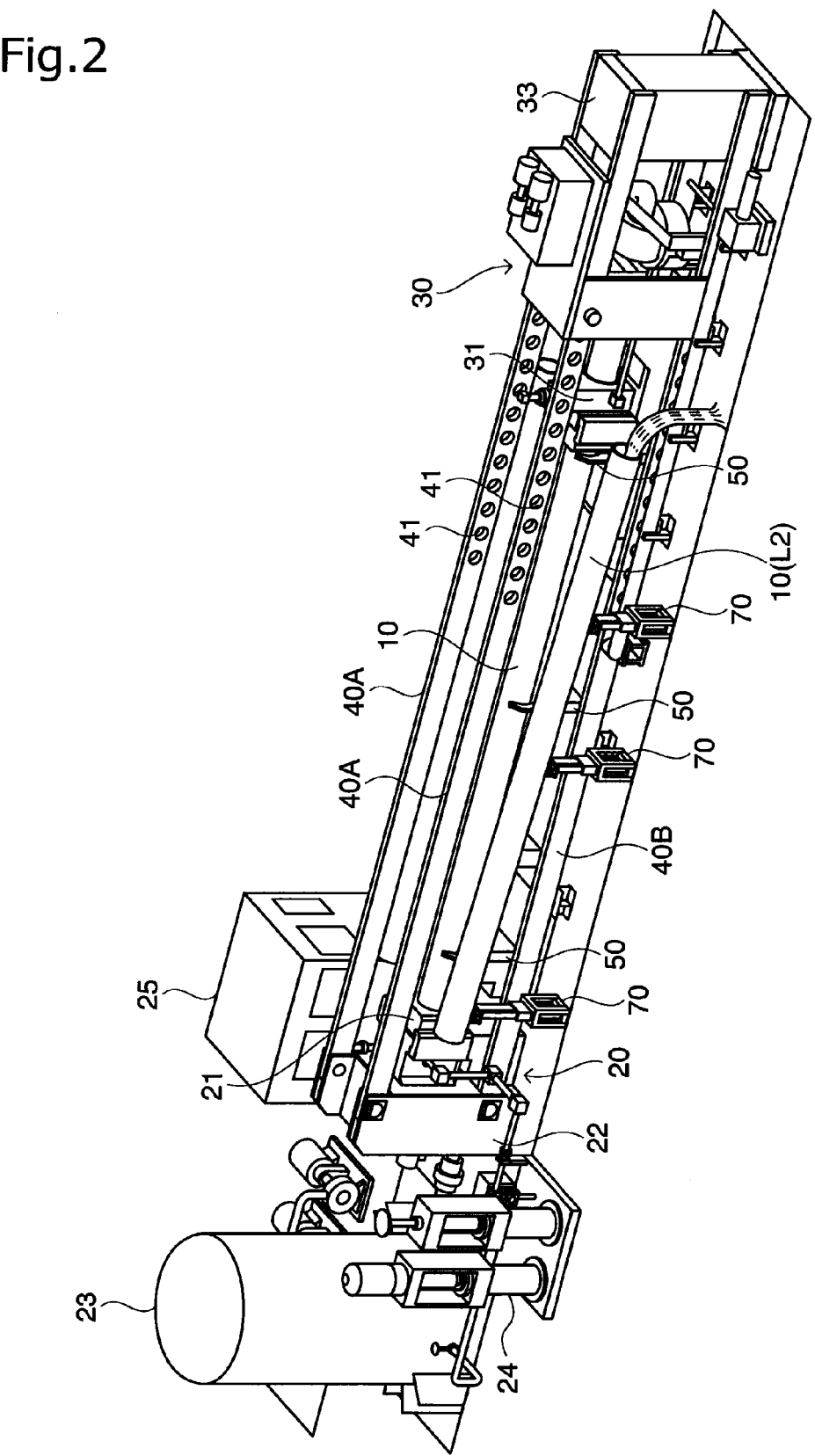
FIG. 2 is a perspective view of the hydraulic pressure tester from another angle.

As shown in perspective views in FIGS. 1 and 2 and schematic three orthogonal views in FIGS. 3(a) to 3(c), the hydraulic pressure tester for the electric resistance welded tube includes a head stock unit 20 disposed on one end side of a tube support line where the electric resistance welded tube 10 (hereafter referred to as "tested tube 10") to be subjected to a hydraulic pressure test is set and a tail stock unit 30 disposed on the other end side of the tube support line. The hydraulic pressure tester checks quality or the like of a welded part (seam part) of the tested tube 10 by pinching the tested tube 10 between both the units 20 and 30 and injecting high-pressure water into the tube.

As shown in FIGS. 1 to 3(c) and FIG. 4, the head stock unit 20 is formed by a head stock main body 21 into which one tube end portion of the tested tube 10 is inserted and which seals the tube end portion and a support body 22 for the head stock main body 21 and both the head stock main body 21 and the support body 22 are integrated with each other and fixedly installed in a fixed position in an electric resistance welded tube manufacturing plant. The head stock unit 20 is combined with a low-pressure water supply tank 23, a high-pressure water supply/discharge mechanism 24, and pipes 26 such as a high-pressure pipe and a low-pressure pipe disposed in a vicinity of the head stock unit 20 to supply and discharge the high-pressure water to and from the tested tube 10. A reference numeral 25 in FIGS. 1, 2, and 4 designates a control room provided in the vicinity of the head stock unit 20 together with the low-pressure water supply tank 23, the high-pressure water supply/discharge mechanism 24, and the like.

On the other hand, as shown in FIGS. 1 to 3(a) and 5, the tail stock unit 30 includes a tail stock main body 31 which can move forward and backward in a longitudinal direction of a tube support line, a pressing device 32 for the tail stock main body 31, and a support body 33 for them. The block-shaped support body 22 of the head stock unit 20 and the block-shaped support body 33 of the tail stock unit 30 are firmly coupled by two horizontal upper beams 40A, 40A on opposite sides and two horizontal lower beams 40B, 40B on opposite sides so that opposite sides between the support bodies 22 and 23 are fully open.

The tail stock pressing device 32 in the tail stock unit 30 is separated from the support body 33 behind the device 32 so as to conform to change in tube length of the tested tube 10 and is placed on a traveling base 34, provided to be movable along the lower beams 40B, 40B on the opposite sides, to thereby move forward and backward along the tube support line together with the tail stock main body 31. By inserting lock pins 42 through engagement holes 41 formed at predetermined intervals in back half portions of the upper beams 40A and the lower beams 40B, the tail stock main body 31 and the tail stock pressing device 32 are fixed in desired positions.

As shown in FIGS. 1 to 3(c) and 5, on the tube support line between the head stock unit 20 and the tail stock unit 30, a plurality of tube clamping devices 50 for supporting the tube are arranged at predetermined intervals in the longitudinal direction. A plurality of horizontal and sliding tube support beams 60 as tube carrier devices for carrying the tested tube 10 into and out of positions on these tube clamping devices 50 are arranged in the longitudinal direction without interfering with the plurality of tube clamping devices 50.

Here, the tube clamping devices 50 are disposed in three positions between the head stock unit 20 and the tail stock unit 30 and the tube clamping device 50 on a side of the head stock is fixedly installed on the lower beams 40B, 40B on the opposite sides. The tube clamping device 50 on a side of the tail stock is mounted onto the traveling base 34 of a traveling movable portion of the tail stock unit 30 and in front of them. The middle tube clamping device 50 is disposed between the lower beams 40B, 40B on the opposite sides and can tilt forward so as not to obstruct forward movement of the traveling movable portion of the tail stock unit 30.

Here, the tube support beams 60 as the tube carrier devices are disposed in two positions between the head stock unit 20 and the tail stock unit 30. The tube support beam 60 on the side of the head stock is disposed in a vicinity of the head stock unit 20. The tube support beam 60 on the side of the tail stock is mounted onto the traveling base 34 of the traveling movable portion of the tail stock unit 30 and between the traveling movable portion and the tube clamping device 50 in front of the traveling movable portion.

As shown in perspective views in FIGS. 6 to 13 and six orthogonal views in FIGS. 14 to 23, each of the tube clamping devices 50 includes a fixed base 51 disposed in a predetermined position in the tube support line between the head stock unit 20 and the tail stock unit 30 and a lifting/lowering base 52 disposed to be able to lift and lower on the fixed base 51. The fixed base 51 is sandwiched between front and back reinforcing plates 51', 51' also functioning as support members and the tube clamping device 50 on the side of the head stock is supported like a bridge between the opposite lower beams 40B, 40B by using one of the reinforcing plates 51', 51' as a support body as shown in the drawings. The middle tube clamping device 50 is disposed between the opposite lower beams 40B, 40B to be able to retreat forward. The tube clamping device 50 on the side of the tail stock is provided onto the traveling base 34 of the traveling movable portion of the tail stock unit 30 (see FIG. 5).

In other words, the tube clamping device 50 on the side of the head stock, the middle tube clamping device 50, and the tube clamping device 50 on the side of the tail stock employ the same structures of the main body portions disposed between the opposite lower beams 40B, 40B and are slightly different from each other in a supporting form. The perspective views in FIGS. 6 to 13 and the six orthogonal views in FIGS. 14 to 23 show the tube clamping device 50 on the side of the head stock and therefore the tube clamping device 50 on the side of the head stock will be taken as an example and details of its structure will be described.

The fixed base 51 of the tube clamping device 50 is a U-shaped frame in a front view. At opposite side portions of the fixed base 51, vertical first cylinders 53, 53 are provided inside the opposite lower beams 40B, 40B. The first cylinders 53, 53 are first drive mechanisms for driving the lifting/lowering base 52 on the fixed base 51. At a middle portion of the fixed base 51 sandwiched between the first cylinders 53, 53, a second cylinder 54 as a second drive mechanism for driving a claw drive body 58 in the lifting/lowering base 52 (described later) is mounted vertically.

The lifting/lowering base 52 is a T-shaped frame in the front view and formed by connecting front and back two face plates 52', 52' at a predetermined interval and a portion excluding an upper portion of the lifting/lowering base 52 is positioned between the opposite first cylinders 53, 53 of the fixed base 51. The upper portion protrudes over the opposite first cylinders 53, 53 and connected to top portions of the first cylinders 53, 53. In this way, the lifting/lowering base 52 is driven for lifting and lowering by the opposite first cylinders 53, 53.

A tube support body 55 for supporting and centering the tested tube 10 is mounted to a central portion of an upper face of the lifting/lowering base 52. The upper face of the tube support body 55 is formed into a V shape for centering of the tested tube 10. Paired opposite turning clamp claws 56, 56 are mounted to opposite overhang portions of the lifting/lowering base 52. The clamp claws 56, 56 are formed into V shapes protruding outward and supported for turning about base portions as fulcrums by support shafts 57, 57 parallel to the tube support line and supported like bridges between the front and back two face plates 52', 52' at the opposite overhang portions of the lifting/lowering base 52. In this way, the clamp claws 56, 56 on the opposite sides can open and close in a vertical plane perpendicular to the tube support line.

In a central portion of the lifting/lowering base 52, the claw drive body 58 for driving the clamp claws 56, 56 for opening and closing is provided independently of the lifting/lowering base 52 so as to freely lift and lower between the front and back two face plates 52', 52'. The claw drive body 58 have opposite side portions connected to the opposite clamp claws 56, 56 by links 59, 59 on inner sides of the centers of turning of the respective base portions and is driven for lifting and lowering by the second cylinder 54 which is the second drive mechanism positioned below the drive body and mounted to the central portion of the lifting/lowering base 52.

In a state in which the lifting/lowering base 52 is at a lowering limit and the claw drive body 58 is at a lifting limit, the clamp claws 56, 56 are fully open to the opposite sides. FIGS. 6 to 8 and 14 to 21 show this fully open state (see FIG. 24). From this state, if the lifting/lowering base 52 lifts, the claw drive body 58 lowers with respect to the lifting/lowering base 52 and, as a result, the clamp claws 56, 56 on the opposite sides turn in closing directions. This is a half open state (see FIG. 25). From this state, if the claw drive body 58 is driven for lowering, the clamp claws 56, 56 on the opposite sides further turn in the closing direction to shift into a fully closed state (clamping). FIGS. 9 to 13, 22, and 23 show this clamping state (see FIG. 26).

The middle tube clamping device 50 disposed between the lower beams 40B, 40B on the opposite sides can tilt forward without interfering with the lower beams 40B, 40B on the opposite sides by bringing the clamp claws 56, 56 on the opposite sides into the fully closed state.

As is specifically shown in FIGS. 3(c) and 5, each of the tube support beams 60 for carrying the tested tube 10 into and out of the position on the tube support body 55 of the tube clamping device 50 is a horizontal beam perpendicular to the tube support line between both the stocks and supported by a guide 61 provided like a bridge between the lower beams 40B, 40B on the opposite sides so as to be able to reciprocate in a horizontal direction perpendicular to the tube support line.

The tube support beam 60 has substantially the same length as the guide 61 and has tube support bodies 62a and 62b on one end portion and the other end portion. Upper faces of the tube support bodies 62a and 62b are formed into V shapes for supporting and centering of the tested tube 10 similarly to the upper face of the tube support body 55 of the lifting/lowering base 52. The tube support beam 60 is driven for reciprocation in the horizontal direction perpendicular to the tube support line by a drive mechanism 63 disposed close to the guide 61. To put it concretely, the one tube support body 62a reciprocates between a tube standby line L1, set on one side of the tube support line for testing the tube between the opposite stocks, and the tube support line and the other tube support body 62b reciprocates between the tube support line, for testing the tube between the opposite stocks, and a drain line L2, set on the other side of the tube support line (see FIG. 3(a)).

On the drain line L2, a plurality of tube support devices 70 (see FIG. 4) are disposed at predetermined intervals along the tube support line so as to support the tested tube 10 along the tube support line. The plurality of tube support devices 70 on the drain line L2 are of a lifting/lowering type, positioned in lower positions than a tube support level by the plurality of tube support beams 60 at lowering limits, positioned in higher positions than the tube support level by the plurality of tube support beams 60 at lifting limits so as to transfer the tested tube 10, and tilt the tested tube 10 downward from the side of the head stock toward the side of the tail stock so as to facilitate discharge of remaining water in the tested tube 10.

The tube support level by the tube support bodies 62a and 62b of the tube support beam 60 is higher than the tube support level by the tube support body 55 when the lifting/lowering base 52 is in the lower limit position and is higher than an upper end level of the clamp claws 56, 56 when the clamp claws 56, 56 of the lifting/lowering base 52 have fully opened to the opposite sides, i.e., when the lifting/lowering base 52 is at the lowering limit and the claw drive body 58 has moved to the lifting limit. The tube support level by the tube support body 52 when the lifting/lowering base 52 has moved to the upper limit position is higher than the tube support level by the tube support bodies 62a and 62b of the tube support beam 60. Incidentally, the tube support level by the tube support body 55 when the lifting/lowering base 52 is in the lower limit position and the upper end level of the clamp claws 56, 56 when the clamp claws 56, 56 of the lifting/lowering base 52 have fully opened to the opposite sides, i.e., when the lifting/lowering base 52 is at the lowering limit and the claw drive body 58 is at the lifting limit are the same.

As shown in FIG. 3(a), the traveling movable portion (the tail stock main body 31 and the tail stock pressing device 32) of the tail stock unit 30 includes tube end sensors 36, 36 on a side of the tube standby line L1. The tube end sensors 36, 36 are mounted to a side face of a front portion of the movable portion at predetermined intervals in a line direction and the traveling movable portion is driven so that a tube end, on the side of the tail stock, of the tested tube 10 carried into the standby line L1 is positioned between the tube end sensors 36, 36. In this way, the traveling movable portion of the tail stock unit 30 is guided, in advance, to a position suitable to an entire length of the tested tube 10 carried into the tube standby line L1.

In this state, a distance between both the stocks is slightly greater than the entire length of the tested tube 10 carried into the tube standby line L1 so that the tested tube 10 can be carried into the tube support line between both the stocks. By pressing the tail stock main body 31 forward from this state, both the stocks are fitted with the opposite end portions of the tested tube 10 to seal the opposite end portions.

Next, the above-described tube clamping device according to the embodiment and an operation and a function of the hydraulic pressure tester using the tube clamping devices will be described.

In a first stage, the one tube support bodies 62a of the plurality of tube support beams 60 are positioned on the tube standby line L1 set on the one side of the tube support line and the other tube support bodies 62b are driven into first positions positioned on the tube support line for the test of the tube between both the stocks (see FIG. 3(c)). Then, the tested tube 10 is carried into the positions on the one tube support bodies 62a of the plurality of tube support beams 60, positioned on the tube standby line L1. At this time, in each of the plurality of tube clamping devices 50, the lifting/lowering base 52 is at the lowering limit and the claw drive body 58 is at the lifting limit as shown in FIG. 24. In other words, the clamp claws 56, 56 are in the fully open state. The plurality of tube support devices 70 on the drain line L2 are at the lowering limits.

In a second stage, the traveling movable portion of the tail stock unit 30 is driven so that the tube end, on the side of the tail stock, of the tested tube 10 carried into the tube standby line L1 is positioned between the tube end sensors 36, 36 (see FIG. 3(a)). In other words, the traveling movable portion of the tail stock unit 30 is guided and fixed in advance into the position suitable to the entire length of the tested tube 10 carried into the tube standby line. In this state, the plurality of tube support beams 60 are synchronously driven into a second position where the one tube support bodies 62a are positioned on the tube support line for the test of the tube between the opposite stocks and the other tube support bodies 62b are positioned on the drain line L2 set on the other side of the tube support line (see FIG. 3(c)). In this way, the tested tube 10 placed on the one tube support bodies 62a of the plurality of tube support beams 60 is carried into the tube support line for the test of the tube between both the stocks.

In a third stage, as shown in FIG. 25, each of the lifting/lowering bases 52 of the plurality of tube clamping devices 50 is driven from the lowering limit to the lifting limit by the first cylinders 53, 53 which are the first drive mechanisms. In this way, the tested tube 10 carried into the tube support line between both the stocks is transferred from positions on the one tube support bodies 62a of the plurality of tube support beams 60 to positions on the respective tube support bodies 55 of the plurality of tube clamping devices 50. At the same time, the clamp claws 56, 56 on the opposite sides of the plurality of tube clamping devices 50 turn from the fully open state into the half open state.

In a fourth stage, as shown in FIG. 26, each of the claw drive bodies 58 of the plurality of tube clamping devices 50 is driven for lowering from the lifting limit toward the lowering limit by the second cylinder 54 as the second drive mechanism. In this way, the clamp claws 56, 56 on the opposite sides of the plurality of tube clamping devices 50 shift into the fully closed state to grasp the tested tube 10 carried into the tube support line with predetermined pressure corresponding to operating pressure of the second cylinder 54 to fix the tested tube 10 onto the support line on their way toward the fully closed state. The plurality of tube support beams 60 return to the original positions (first positions) and the next tested tube 10 is placed on the one tube support bodies 62a.

In a fifth stage, the tail stock pressing device 32 of the traveling movable portion of the tail stock unit 30 is actuated to push out the tail stock main body 32. In this way, the one tube end portion of the tested tube 10 carried into the tube support line between both the stocks is pushed into the head stock main body 21 of the headstock unit 20 and the other tube end portion of the tested tube 10 is pushed into the tail stock main body 31 of the tail stock unit 30. As a result, the opposite tube ends of the tested tube 10 are sealed with both the stocks.

In a sixth stage, first, from the low-pressure water supply tank 23 disposed in the vicinity of the head stock unit 20, the low-pressure water is injected into the tested tube 10 to fill it up at once through the head stock main body 21 of the head stock unit 20. Then, by operation of the high-pressure water supply/discharge mechanism 24, high-pressure water is injected into the tested tube 10 through the head stock main body 21. Discharge of air in the tube as a result of the injection of the low-pressure water is carried out through the tail stock main body 31 of the tail stock unit 30. When the inside of the tested tube 10 is filled with the low-pressure water, an exhaust valve in the tail stock main body 31 is switched from an open state to a closed state.

Although the tested tube 10 expands in a radial direction due to the injection of the high-pressure water into the tested tube 10, the expansion is absorbed by turning of the opposite clamp claws 56, 56 of the plurality of tube clamping devices 50 in opening directions against closing forces due to lowering of the claw drive bodies 58.

In a seventh stage, by operation of the high-pressure water supply/discharge mechanism 24, the high-pressure water in the tested tube 10 is discharged to an outside of the tube through the head stock main body 21 of the head stock unit 20 and recovered. Then, the tail stock pressing device 32 of the traveling movable portion of the tail stock unit 30 is actuated in a reverse direction and the tail stock main body 32 retreats to the original position. In this way, the one tube end portion of the tested tube 10 comes out of the head stock main body 21 of the head stock unit 20 and the other tube end portion of the tested tube 10 comes out of the tail stock main body 31 of the tail stock unit 30.

In an eighth stage, each of the claw drive bodies 58 of the plurality of tube clamping devices 50 is driven to the lifting limit by the second cylinder 54 which is the second drive mechanism. In this way, the clamp claws 56, 56 on the opposite sides return into the half open state to release the tested tube 10 from constraint. Then, the lifting/lowering bases 52 of the plurality of tube clamping devices 50 return to the lowering limits. As a result, the clamp claws 56, 56 on the opposite sides of the plurality of tube clamping devices 50 return into the fully open state and the tested tube 10 which has finished the high-pressure water test is transferred from the positions on the respective tube support bodies 55 of the plurality of tube clamping devices 50 to the positions on the other tube support bodies 62b of the plurality of tube support beams 60.

In a ninth stage, the plurality of tube support beams 60 are synchronously driven into the second position where the one tube support bodies 62a are positioned on the tube support line for the test of the tube between the opposite stocks and the other tube support bodies 62b are positioned on the drain line set on the other side of the tube support line. In this way, the tested tube 10 which has finished the test is discharged from the tube support line between both the stocks to the drain line L2 on the side and the next tested tube 10 placed on the one tube support bodies 62a are carried into the tube support line between both the stocks.

The tested tube 10 carried into the tube support line between both the stocks is subjected to the high-pressure water test in the same way as that described above. On the drain line L2, the plurality of tube support devices 70 are driven from the lowering limit to the lifting limit. In this way, the tested tube 10 after the test and discharged to the drain line L2 is transferred from the positions on the other tube support bodies 62b of the plurality of tube support beams 60 to the positions on the plurality of tube support devices 70 and supported while inclined downward from the side of the head stock toward the side of the tail stock. As a result, remaining water in the tube is discharged and removed and then the tested tube 10 is carried out of the drain line L2.

When the transfer of the tube to the positions on the respective tube support bodies 55 of the plurality of tube clamping devices 50 and the transfer of the tube to the positions on the plurality of tube support devices 70 are finished, the plurality of tube support beams 60 return again to the original positions so as to receive the next tested tube 10.

By repeating this process, the high-pressure water tests of the tested tubes 10 are carried out continuously. In each of the plurality of tube clamping devices 50 for fixing the tested tube 10 onto the tube support line between both the stocks, a lowering stroke of the claw drive body 58 necessary for closing operations of the clamp claws 56, 56 is partially born by the lifting of the lifting/lowering base 52 in transferring the tested tube 10 and therefore the lowering stroke of the claw drive body 58 for opening and closing the clamp claws 56, 56 can be suppressed. As a result, the height of each of the tube clamping devices 50 can be suppressed.

Moreover, by combining the lifting of the lifting/lowering base 52 and the lowering of the claw drive body 58 in the tube clamping device 50, it is possible to open the clamp claws 56, 56 wide toward the opposite sides. In this way, it is easy to hand and receive the tested tube 10 to and from the tube support body 55 of the tube clamping device 50. Because the lifting stroke of the lifting/lowering base 52 is suppressed, the height of the tube clamping device 50 is suppressed. At this time, although the clamp claws 56, 56 open wide toward the opposite sides, the lowering stroke of the claw drive body 58 in the closing operating is suppressed and therefore increase in size of the tube clamping device 50 is avoided as described above.

Because the tube clamping devices 50 according to the embodiment and used for the hydraulic pressure tester according to the embodiment are compact and have simple structures, the hydraulic pressure tester itself is compact and lightweight and has a simple structure.

EXPLANATION OF REFERENCE NUMERALS 10 tested tube
20 head stock unit
21 head stock main body
22 head stock support body
23 low-pressure water supply tank
24 high-pressure water supply/discharge mechanism
25 pipes
30 tail stock unit
31 tail stock main body
32 tail stock pressing device
33 tail stock support body
34 traveling base
36 tube end sensor
40A upper beam
40B lower beam
41 engagement hole
42 lock pin
50 tube clamping device
51 fixed base
51' reinforcing plate
52 lifting/lowering base
52' face plates
53 first cylinder (first drive mechanism)
54 second cylinder (second drive mechanism)
55 tube support body
56 clamp claw
57 support shaft
58 claw drive body
59 link
60 tube support beam
61 guide
62a, 62b tube support body
63 drive mechanism
70 tube support device
L1 tube standby line
L2 drain line

The invention claimed is:

1. A tube clamping device comprising:
a fixed base installed on a tube treatment line;
a lifting/lowering base provided onto the fixed base to be able to lift and lower and including a tube support body for supporting and centering a tube on itself;
a first drive mechanism mounted to the fixed base so as to drive the lifting/lowering base for lifting and lowering;
paired opposite clamp claws mounted in positions, between which the tube support body of the lifting/lowering base is sandwiched, to be able to turn so as to clamp the tube supported on the tube support body;
a lifting/lowering claw drive body provided in the lifting/lowering base so as to lift and lower independently of the lifting/lowering base and having opposite side portions connected to the opposite clamp claws by links so as to turn the clamp claws on opposite sides of the lifting/lowering base in closing directions by lowering with respect to the lifting/lowering base; and
a second drive mechanism mounted to the fixed base so as to drive the claw drive body for lifting and lowering.

2. The tube clamping device according claim 1,
wherein the opposite clamp claws fully open with the lifting/lowering base being positioned at a lowering limit and the claw drive body being positioned at a lifting limit and the opposite clamp claws are positioned at the same level as the tube support body between the clamp claws in the fully open state.

3. The tube clamping device according to claim 2,
wherein the lifting/lowering base is driven from the lowering limit to a lifting limit with the claw drive body being positioned at the lifting limit, so that the claw drive body lowers with respect to the lifting/lowering base to drive the opposite clamp claws for turning into a half open state.

4. The tube clamping device according to claim 3,
wherein the claw drive body lowers from the lifting limit with the lifting/lowering base being driven from the lowering limit to the lifting limit, so that the opposite clamp claws further close to clamp the tube on the tube support body irrespective of a tube diameter.

5. A hydraulic pressure tester for pinching a manufactured tube between a head stock, for sealing a tube end and injecting and discharging high-pressure water, and a tail stock, for sealing a tube end, and injecting the high-pressure water into the tube, wherein the tube clamping devices according to claim 1 is arranged, as tube support mechanisms between the head stock and the tail stock, in a longitudinal direction between both the stocks.

6. The hydraulic pressure tester according to claim 5,
wherein support bodies of the head stock and the tail stock are coupled by an upper beam and a lower beam so that opposite sides of a tube support line between the opposite stocks are open.

7. The hydraulic pressure tester according to claim 6,
wherein horizontal tube support beams orthogonal to the tube support line between the head stock and the tail stock and for sliding in the orthogonal direction are disposed in a plurality of positions between both the stocks so as not to interfere with the tube clamping devices between both the stocks so as to carry the tube into and out of the tube support line between both the stocks, a tube support level by the plurality of tube support beams is higher than a tube support level by the tube support bodies of the tube clamping devices, and each of the tube support bodies moves from the lowering limit to the lifting limit together with the lifting/lowering base, so that the tube support level by the tube support bodies of the tube clamping devices becomes higher than the tube support level by the plurality of tube support beams.

8. The hydraulic pressure tester according to claim 7,
wherein each of the tube support beams has tube support bodies for supporting and centering the tube on themselves in at least two positions in a longitudinal direction.

9. The hydraulic pressure tester according to claim 6,
wherein the head stock is fixed and the tail stock is movable in a front-back direction of the tube support line between both the stocks.

10. The hydraulic pressure tester according to claim 9,
wherein the tail stock includes a detecting mechanism for a tube end, on a side of the tail stock, of the tube on standby beside the tube support line between both the stocks and is guided in advance to a moving position corresponding to a detected tube end position.

11. The hydraulic pressure tester according to claim 9, wherein the tube clamping device is fixedly installed behind the head stock, the tube clamping device is provided to be movable with the tail stock in front of the tail stock, and one or the plurality of tube clamping device(s) is (are) disposed between the fixed tube clamping device on the side of the head stock and the movable tube clamping device on the side of the tail stock.

12. The hydraulic pressure tester according to claim 11, wherein at least one tube clamping device on the side of the tail stock out of the one or the plurality of tube clamping device(s) disposed between the fixed tube clamping device on the side of the head stock and the movable tube clamping device on the side of the tail stock can tilt to a receding position so as not to obstruct forward movement of a movable portion on the side of the tail stock.

* * * * *